United States Patent
Coakley et al.

(10) Patent No.: US 10,675,176 B1
(45) Date of Patent: Jun. 9, 2020

(54) TREATMENT SYSTEMS, DEVICES, AND METHODS FOR COOLING TARGETED TISSUE

(71) Applicant: Zeltiq Aesthetics, Inc., Pleasanton, CA (US)

(72) Inventors: Joseph Coakley, Dublin, CA (US); William P. Pennybacker, Livermore, CA (US); Bryan J. Weber, Livermore, CA (US)

(73) Assignee: Zeltiq Aesthetics, Inc., Pleasanton, CA (US)

(*) Notice: Subject to any disclaimer, the term of this patent is extended or adjusted under 35 U.S.C. 154(b) by 598 days.

(21) Appl. No.: 14/662,181

(22) Filed: Mar. 18, 2015

Related U.S. Application Data

(60) Provisional application No. 61/955,723, filed on Mar. 19, 2014.

(51) Int. Cl.
*A61F 7/00* (2006.01)

(52) U.S. Cl.
CPC .............. *A61F 7/0085* (2013.01); *A61F 7/00* (2013.01); *A61F 2007/0041* (2013.01); *A61F 2007/0056* (2013.01)

(58) Field of Classification Search
CPC .. A61F 7/0085; A61F 7/00; A61F 2007/0056; A61F 2007/0041; A61F 5/0125; A61F 2005/0167; A61F 2005/0179; A61B 90/50
See application file for complete search history.

(56) References Cited

U.S. PATENT DOCUMENTS

| | | | |
|---|---|---|---|
| 681,806 | A | 9/1901 | Mignault et al. |
| 889,810 | A | 6/1908 | Robinson et al. |
| 1,093,868 | A | 4/1914 | Leighty |
| 2,516,491 | A | 7/1950 | Swastek |
| 2,521,780 | A | 9/1950 | Dodd et al. |
| 2,726,658 | A | 12/1955 | Chessey |
| 2,766,619 | A | 10/1956 | Tribus et al. |
| 2,851,602 | A | 9/1958 | Cramwinckel et al. |

(Continued)

FOREIGN PATENT DOCUMENTS

| | | |
|---|---|---|
| AU | 2011253768 A1 | 6/2012 |
| CA | 2441489 A1 | 3/2005 |

(Continued)

OTHER PUBLICATIONS

ThermaCool Monopolar Capacitive Radiofrequency, The one choice for nonablative tissue tightening and contouring, Thermage, Inc. Tech Brochure, Nov. 30, 2005, 8 pgs.

(Continued)

*Primary Examiner* — Kaitlyn E Smith
*Assistant Examiner* — Yasamin Ekrami
(74) *Attorney, Agent, or Firm* — Perkins Coie LLP

(57) ABSTRACT

Treatment systems include conformable applicators for performing cryotherapy are described. Aspects of the technology are further directed to methods and conformable applicators capable of affecting target regions. The conformable applicators can be applied a wide range of treatment sites. A strap assembly can hold applicator against the treatment site, and a holder assembly can be adhered to the subject's skin to inhibit, limit, or substantially prevent movement of the applicator along the subject's skin.

12 Claims, 13 Drawing Sheets

(56) References Cited

U.S. PATENT DOCUMENTS

| | | |
|---|---|---|
| 3,093,135 A | 6/1963 | Hirschhorn |
| 3,132,688 A | 5/1964 | Nowak |
| 3,133,539 A | 5/1964 | Eidus et al. |
| 3,282,267 A | 11/1966 | Eidus |
| 3,502,080 A | 3/1970 | Hirschhorn |
| 3,587,577 A | 6/1971 | Zubkov et al. |
| 3,591,645 A | 7/1971 | Selwitz |
| 3,692,338 A | 9/1972 | Nick |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A * | 10/1990 | Golden ............... A61F 7/02 165/46 |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,324,318 A * | 6/1994 | Smith ............... A61F 7/10 607/104 |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelgat et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A * | 9/1998 | Strauss ............. A41D 13/0025 62/259.3 |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |

(56) References Cited

U.S. PATENT DOCUMENTS

| | | |
|---|---|---|
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B2 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |

(56) References Cited

U.S. PATENT DOCUMENTS

| | | |
|---|---|---|
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1* | 4/2002 | Palmer ............... A61B 17/3417 606/1 |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |

(56) References Cited

U.S. PATENT DOCUMENTS

| | | |
|---|---|---|
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1* | 12/2005 | Carlsmith ............ A41D 13/065 602/20 |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1* | 3/2008 | Levinson ................. A61F 7/10 607/108 |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |

(56) References Cited

U.S. PATENT DOCUMENTS

| | | |
|---|---|---|
| 2012/0209363 A1 | 8/2012 | Williams, III et al. |
| 2012/0233736 A1* | 9/2012 | Tepper .............. A41D 13/0153 2/24 |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2012/0325221 A1* | 12/2012 | Tran .................... A62B 18/025 128/206.17 |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron Edoute et al. |
| 2013/0245507 A1 | 9/2013 | Khorassani Zadeh |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1* | 3/2014 | Levinson ................ A61F 7/10 607/96 |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1* | 9/2014 | Biser .................... A61F 7/02 607/104 |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0317240 A1* | 11/2016 | Vogele .................. A61B 90/18 |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'neil et al. |
| 2018/0185189 A1 | 7/2018 | Weber et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |

(56) References Cited

FOREIGN PATENT DOCUMENTS

| | | |
|---|---|---|
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.

Al-Sakere, B. et al. "Tumor Ablation with Irreversible Electroporation," PLoS One, Issue 11, Nov. 2007, 8 pages.

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.

Ardevol, A. et al., "Cooling Rates of Tissue Samples During Freezing with Liquid Nitrogen," Journal of Biochemical and Biophysical Methods, vol. 27, 1993, pp. 77-86.

Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.

Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.

Bohm, T. et al., "Saline-Enhanced Radiofrequency Ablation of Breast Tissue: an in Vitro Feasibility Study," Investigative Radiology, vol. 35 (3), 2000, pp. 149-157.

Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.

Burge, S.M. et al., "Hair Follicle Destruction and Regeneration in Guinea Pig Skin after Cutaneous Freeze Injury," Cryobiology, 27(2), 1990, pp. 153-163.

Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.

Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.

Donski, P. K. et al., "The Effects of Cooling no. Experimental Free Flap Survival," British Journal of Plastic Surgery, vol. 33, 1980, pp. 353-360.

Duck, F. A., Physical Properties of Tissue, Academic Press Ltd., chapters 4 & 5, 1990, pp. 73-165.

Duncan, W. C. et al., "Cold Panniculitis," Archives of Dermatology, vol. 94, Issue 6, Dec. 1966, pp. 722-724.

Epstein, E. H. et al., "Popsicle Panniculitis," The New England Journal of Medicine, 282(17), Apr. 23, 1970, pp. 966-967.

Fournier, L. et al. "Lattice Model for the Kinetics of Rupture of Fluid Bilayer Membranes," Physical Review, vol. 67, 2003, pp. 051908-1-051908-11.

(56) References Cited

OTHER PUBLICATIONS

Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.

Gage, A. "Current Progress in Cryosurgery," Cryobiology 25, 1988, pp. 483-486.

Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].

Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.

Heller Page, E. et al., "Temperature-dependent skin disorders," Journal of the American Academy of Dermatology, vol. 18, No. 5, Pt 1, May 1988, pp. 1003-1019.

Hemmingsson, A. et al. "Attenuation in Human Muscle and Fat Tissue in Vivo and in Vitro," Acra Radiologica Diagnosis, vol. 23, No. 2, 1982, pp. 149-151.

Henry, F. et al., "Les Dermatoses Hivernales," Rev Med Liege, 54:11, 1999, pp. 864-866. [Abstract Attached].

Hernan, P. et al., "Study for the evaluation of the efficacy of Lipocryolysis (EEEL)", Nov. 30, 2011.

Hernan, R. P., "A Study to Evaluate the Action of Lipocryolysis", 33(3) CryoLellers, 2012, pp. 176-180.

Holland, DB. et al. "Cold shock induces the synthesis of stress proteins in human keratinocytes," PubMed Journal of Investigative Dermatology; 101(2): Aug. 1993, pp. 196-199.

Holman, W. L. et al., "Variation in Cryolesion Penetration Due to Probe Size and Tissue Thermal Conductivity," The Annals of Thoracic Surgery, vol. 53, 1992, pp. 123-126.

Hong, J.S. et al., "Patterns of Ice Formation in Normal and Malignant Breast Tissue," Cryobiology 31, 1994, pp. 109-120.

Huang et al. "Comparative Proteomic Profiling of Murine Skin," Journal of Investigative Dermatology, vol. 121(1), Jul. 2003, pp. 51-64.

Isambert, H. "Understanding the Electroporation of Cells and Artificial Bilayer Membranes," Physical Review Letters, vol. 80, No. 15, 1998, pp. 3404-3707.

Jalian, H. R. et al., "Cryolipolysis: A Historical Perspective and Current Clinical Practice", 32(1) Semin. Cutan. Med. Surg., 2013, pp. 31-34.

Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.

Koska, J. et al., "Endocrine Regulation of Subcutaneous Fat Metabolism During Cold Exposure in Humans," Annals of the New York Academy of Sciences, vol. 967, 2002, pp. 500-505.

Kundu, S. K. et al., "Breath Acetone Analyzer: Diagnostic Tool to Monitor Dietary Fat Loss," Clinical Chemistry, vol. 39, Issue (1), 1993, pp. 87-92.

Kundu, S. K. et al., "Novel Solid-Phase Assay of Ketone Bodies in Urine," Clinical Chemistry, vol. 37, Issue (9), 1991, pp. 1565-1569.

Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.

Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.

Levchenko et al., "Effect of Dehydration on Lipid Metabolism" Ukrainskii Biokhimicheskii Zhurnal, vol. 50, Issue 1, 1978, pp. 95-97.

Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.

Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.

L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.

Maize, J.C. "Panniculitis," Cutaneous Pathology, Chapter 13, 1998, 327-344.

Malcolm, G. T. et al., "Fatty Acid Composition of Adipose Tissue in Humans: Differences between Subcutaneous Sites," The American Journal of Clinical Nutrition, vol. 50, 1989, pp. 288-291.

Manstein, D. et al. "A Novel Cryotherapy Method of Non-invasive, Selective Lipolysis," LasersSurg.Med 40:S20, 2008, p. 104.

Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.

Mayoral, "Case Reports: Skin Tightening with a Combined Unipolar and Bipolar Radiofrequency Device," Journal of Drugs in Dermatology, 2007, pp. 212-215.

Mazur, P. "Cryobiology: the Freezing of Biological Systems," Science, 68, 1970, pp. 939-949.

Merrill, T. "A Chill to the Heart: A System to Deliver Local Hypothermia Could One Day Improve the Lives of Heart-Attack Patients," Mechanical Engineering Magazine, Oct. 2010, 10 pages.

Miklavcic, D. et al. "Electroporation-Based Technologies and Treatments," The Journal of Membrane Biology (2010) 236:1-2, 2 pgs.

Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.

Murphy, J. V. et al., "Frostbite: Pathogenesis and Treatment" The Journal of Trauma: Injury, Infection, and Critical Care, vol. 48, No. 1, Jan. 2000, pp. 171-178.

Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.

Nagle, W. A. et al. "Cultured Chinese Hamster Cells Undergo Apoptosis After Exposure to Cold but Nonfreezing Temperatures," Cryobiology 27, 1990, pp. 439-451.

Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.

Nanda, G.S. et al., "Studies on electroporation of thermally and chemically treated human erythrocytes," Bioelectrochemistry and Bioenergetics, 34, 1994, pp. 129-134, 6 pgs.

Narins, D.J. et al. "Non-Surgical Radiofrequency Facelift", The Journal of Drugs in Dermatology, vol. 2, Issue 5, 2003, pp. 495-500.

Nielsen, B. "Thermoregulation in Rest and Exercise," Acta Physiologica Scandinavica Supplementum, vol. 323 (Copenhagen 1969), pp. 7-74.

Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.

Nurnberger, F. "So-Called Cellulite: An Invented Disease," Journal of Dermatologic Surgery and Oncology, Mar. 1978, pp. 221-229.

Pease, G. R. et al., "An Integrated Probe for Magnetic Resonance Imaging Monitored Skin Cryosurgery," Journal of Biomedical Engineering, vol. 117, Feb. 1995, pp. 59-63.

Pech, P. et al., "Attenuation Values, Volume Changes and Artifacts in Tissue Due to Freezing," Acta Radiologica ,vol. 28, Issue 6, 1987, pp. 779-782.

Peterson, L. J. et al., "Bilateral Fat Necrosis of the Scrotum," Journal of Urology, vol. 116, 1976, pp. 825-826.

Phinney, S. D. et al., "Human Subcutaneous Adipose Tissue Shows Site-Specific Differences in Fatty Acid Composition," The American Journal of Clinical Nutrition, vol. 60, 1994, pp. 725-729.

Pierard, G.E. et al., "Cellulite: From Standing Fat Herniation to Hypodermal Stretch Marks," The American Journal of Dermatology, vol. 22, Issue 1, 2000, pp. 34-37, [Abstract].

(56) References Cited

OTHER PUBLICATIONS

Pope, K. et al. "Selective Fibrous Septae Heating: An Additional Mechanism of Action for Capacitively Coupled Monopolar Radiofrequency" Thermage, Inc. Article, Feb. 2005, 6pgs.

Quinn, P. J. "A Lipid-Phase Separation Model of Low-Temperature Damage to Biological Membranes," Cryobiology, 22, 1985, 128-146.

Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.

Renold, A.E. et al. "Adipose Tissue" in Handbook of Physiology, Chapter 15, (Washington, D.C., 1965) pp. 169-176.

Rossi, A. B. R. et al. "Cellulite: a Review," European Academy of Dermatology and Venercology, 2000, pp. 251-262, 12 pgs.

Rubinsky, B. "Principles of Low Temperature Cell Preservation," Heart Failure Reviews, vol. 8, 2003, pp. 277-284.

Rubinsky, B. et al., "Cryosurgery: Advances in the Application of low Temperatures to Medicine," International Journal of Refrigeration, vol. 14, Jul. 1991, pp. 190-199.

Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.

Schoning, P. et al., "Experimental Frostbite: Freezing Times, Rewarming Times, and Lowest Temperatures of Pig Skin Exposed to Chilled Air," Cryobiology 27, 1990, pp. 189-193.

Shephard, R. J. "Adaptation to Exercise in the Cold," Sports Medicine, vol. 2, 1985, pp. 59-71.

Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.

Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.

Thermage, News Release, "Study Published in Facial Plastic Surgery Journal Finds Selective Heating of Fibrous Septae Key to Success and Safety of Thermage ThermaCool System," Jun. 20, 2005, 2 pages.

Vallerand et al. "Cold Stress Increases Lipolysis, FFA Ra and TG/FFA Cycling in Humans," Aviation, Space, and Environmental Medicine 70(1), 1999, pp. 42-50.

Wang, X. et al., "Cryopreservation of Cell/Hydrogel Constructs Based on a new Cell-Assembling Technique," Sep. 5, 2009, 40 pages.

Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.

Winkler, C. et al., "Gene Transfer in Laboratory Fish: Model Organisms for the Analysis of Gene Function," in Transgenic Animals, Generation and Use (The Netherlands 1997), pp. 387-395.

Young, H. E. et al. "Isolation of Embryonic Chick Myosatellite and Pluripotent Stem Cells" The Journal of Tissue Culture Methods, vol. 14, Issue 2, 1992, pp. 85-92.

Zelickson, B. et al., "Cryolipolysis for Noninvasive Fat Cell Destruction: Initial Results from a Pig Model", 35 Dermatol. Sug., 2009, pp. 1-9.

Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

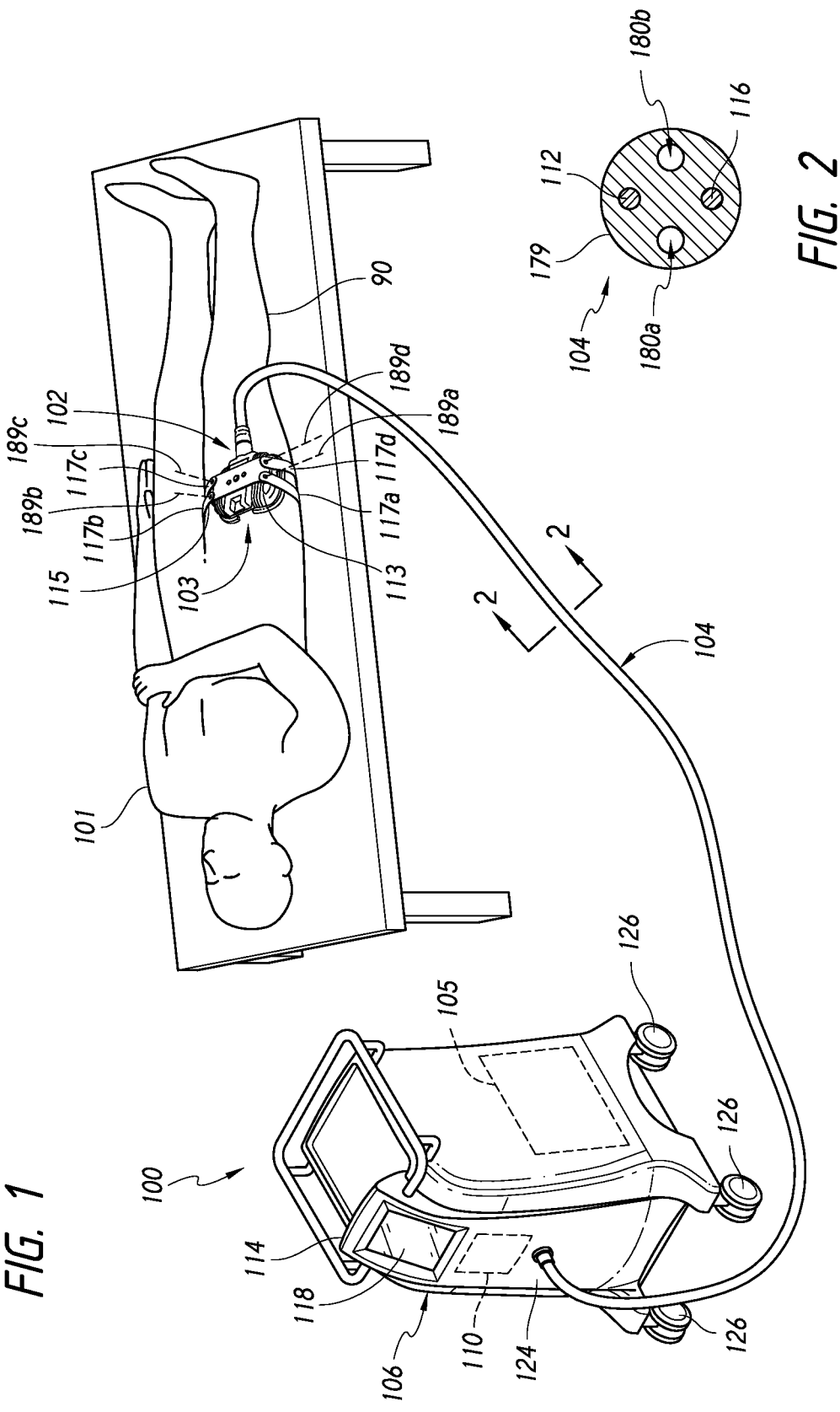

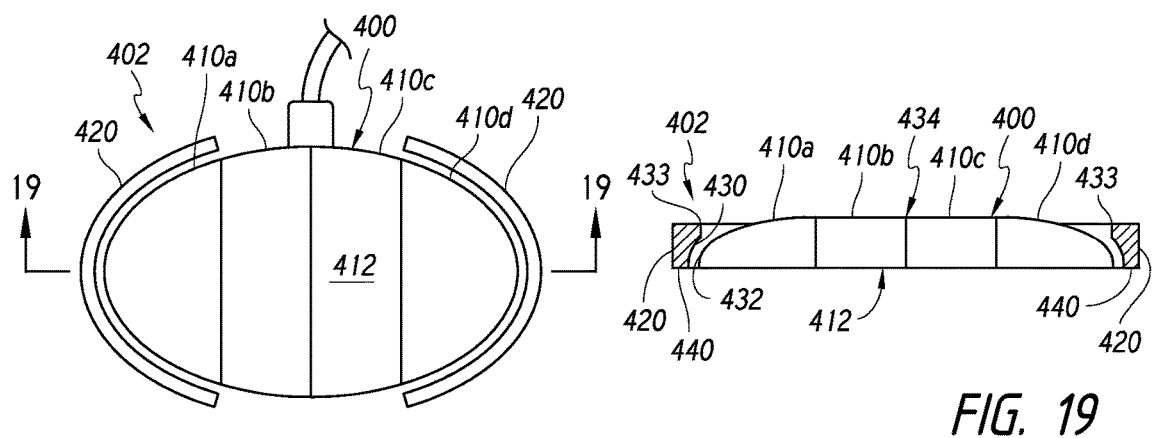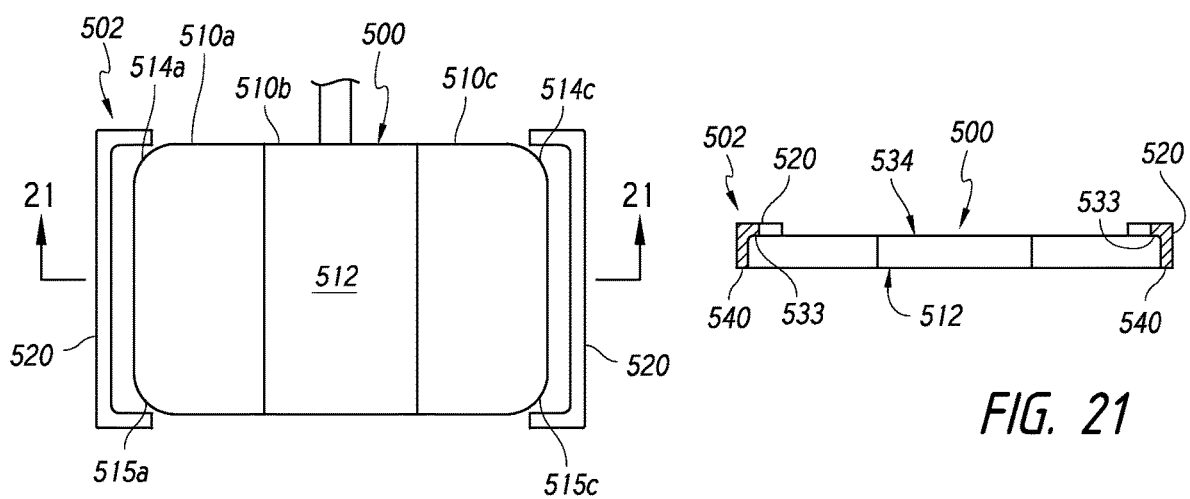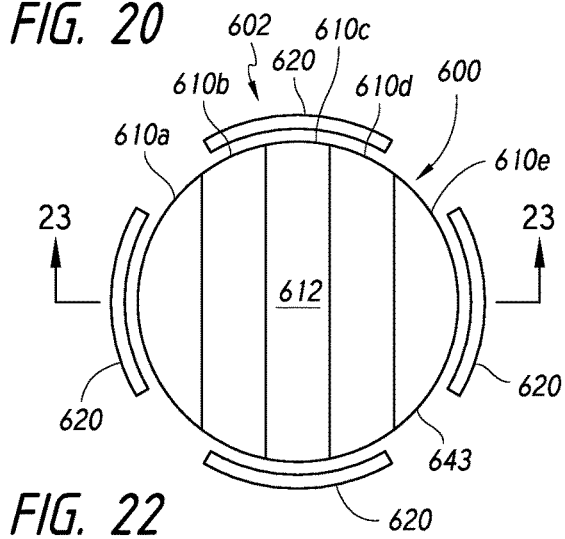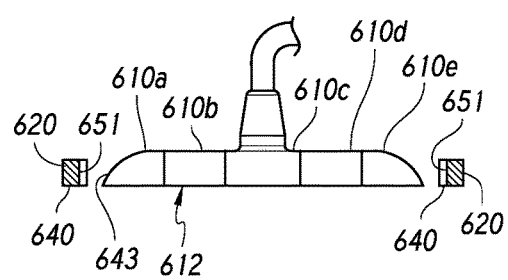

TREATMENT SYSTEMS, DEVICES, AND METHODS FOR COOLING TARGETED TISSUE

CROSS-REFERENCE TO RELATED APPLICATION

The present application claims priority under 35 U.S.C. § 119(e) to U.S. Provisional Application Ser. No. 61/955,723, filed Mar. 19, 2014, the disclosure of which is incorporated herein by reference in its entirety.

INCORPORATION BY REFERENCE OF COMMONLY-OWNED APPLICATIONS AND PATENTS

The following commonly assigned U.S. Patent Applications and U.S. Patents are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Patent Publication No. 2011/0066216 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Provisional Patent Application Ser. No. 60/941,567 entitled "METHODS, APPARATUSES AND SYSTEMS FOR COOLING THE SKIN AND SUBCUTANEOUS TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Patent Publication No. 2010/0152824 entitled "SYSTEMS AND METHODS WITH INTERRUPT/RESUME CAPABILITIES FOR COOLING SUBCUTANEOUS LIPID-RICH CELLS";

U.S. Pat. No. 8,192,474 entitled "TISSUE TREATMENT METHODS";

U.S. Patent Publication No. 2010/0280582 entitled "DEVICE, SYSTEM AND METHOD FOR REMOVING HEAT FROM SUBCUTANEOUS LIPID-RICH CELLS";

U.S. Patent Publication No. 2012/0022518 entitled "COMBINED MODALITY TREATMENT SYSTEMS, METHODS AND APPARATUS FOR BODY CONTOURING APPLICATIONS";

U.S. Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. patent application Ser. No. 13/830,413 entitled "MULTI-MODALITY TREATMENT SYSTEMS, METHODS AND APPARATUS FOR ALTERING SUBCUTANEOUS LIPID-RICH TISSUE";

U.S. patent application Ser. No. 13/830,027 entitled "TREATMENT SYSTEMS WITH FLUID MIXING SYSTEMS AND FLUID-COOLED APPLICATORS AND METHODS OF USING THE SAME";

U.S. patent application Ser. No. 11/528,225 entitled "COOLING DEVICE HAVING A PLURALITY OF CONTROLLABLE COOLING ELEMENTS TO PROVIDE A PREDETERMINED COOLING PROFILE;"

U.S. Pat. No. 8,285,390 entitled "MONITORING THE COOLING OF SUBCUTANEOUS LIPID-RICH CELLS, SUCH AS THE COOLING OF ADIPOSE TISSUE,"

U.S. patent application Ser. No. 14/611,127 entitled "TREATMENT SYSTEMS, METHODS, AND APPARATUS FOR IMPROVING THE APPEARANCE OF SKIN AND PROVIDING FOR OTHER TREATMENTS,"

U.S. patent application Ser. No. 14/610,807 entitled "COMPOSITIONS, TREATMENT SYSTEMS AND METHODS FOR IMPROVED COOLING OF LIPID-RICH TISSUE,"

U.S. patent application Ser. No. 14/611,052 entitled "TREATMENT SYSTEMS AND METHODS FOR TREATING CELLULITE AND FOR PROVIDING OTHER TREATMENTS," and International Patent Application No. PCT/US2015/013,971 entitled "TREATMENT SYSTEMS AND METHODS FOR AFFECTING GLANDS AND OTHER TARGETED STRUCTURES."

TECHNICAL FIELD

The present disclosure relates generally to treatment systems, devices, and methods for removing heat from a subject. In particular, several embodiments are directed to treatment systems, conformable applicators, and methods for holding applicators for enhanced cooling of targeted tissue.

BACKGROUND

Excess body fat, or adipose tissue, may be present in various locations of the body, including, for example, the thighs, buttocks, abdomen, knees, back, face, arms, and other areas. Excess adipose tissue can detract from personal appearance and athletic performance. Moreover, excess adipose tissue is thought to magnify the unattractive appearance of cellulite, which forms when subcutaneous fat lobules protrude or penetrate into the dermis and create dimples where the skin is attached to underlying structural fibrous strands. Cellulite and excessive amounts of adipose tissue are often considered to be cosmetically unappealing. For example, excess adipose tissue located at a subject's outer thighs can form "saddlebags," and excess adipose tissue at the sides of the subject's waistline can form "love-handles" or a "muffin top." Diet and exercise may be insufficient to significantly reduce such excess adipose tissue.

Aesthetic improvement of the human body often involves the selective removal of adipose tissue. Currently, the most common procedures for this purpose are invasive, such as liposuction or other surgical techniques. Invasive procedures, however, tend to be associated with high cost, long recovery times, and increased risk of complications. In many instances, non-invasive or minimally invasive procedures can allow some or all of these disadvantages to be avoided while providing at least comparable clinical outcomes as those of invasive procedures. For example, non-invasive removal of excess subcutaneous adipose tissue can eliminate both unnecessary recovery time and discomfort associated with invasive procedures, such as liposuction. Conventional non-invasive treatments for removing excess body fat typically include application of topical agents, use of weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option if, as another example, they cause an allergic or negative reaction. Furthermore, fat loss in selective areas (e.g., inner or outer regions of the thighs) of a person's body often cannot be achieved using general or systemic weight-loss methods.

Other methods designed to reduce subcutaneous adipose tissue include laser-assisted liposuction and mesotherapy. Non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. Additional methods and devices for non-invasively reducing subcutaneous adipose tissue by cooling are disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

In the drawings, identical reference numbers identify similar elements or acts.

FIG. 1 is a partially schematic, isometric view of a treatment system for non-invasively affecting subcutaneous target regions of a subject in accordance with an embodiment of the technology.

FIG. 2 is a cross-sectional view of a connector of the treatment system of FIG. 1 in accordance with embodiments of the technology.

FIG. 18 is a bottom view of an applicator and an applicator holder assembly in accordance with various embodiments of the present technology.

FIG. 19 is a schematic cross-sectional view of the applicator and holder assembly taken along line 19-19 of FIG. 18.

FIG. 20 is a bottom view of an applicator and an applicator holder assembly in accordance with various embodiments of the present technology.

FIG. 21 is a schematic cross-sectional view of the holder assembly taken along line 21-21 of FIG. 20.

FIG. 22 is a bottom view of an applicator and an applicator holder assembly in accordance with various embodiments of the present technology.

FIG. 23 is a schematic cross-sectional view of the applicator and holder assembly taken along line 23-23 of FIG. 22.

DETAILED DESCRIPTION

A. Overview

Figure 3:
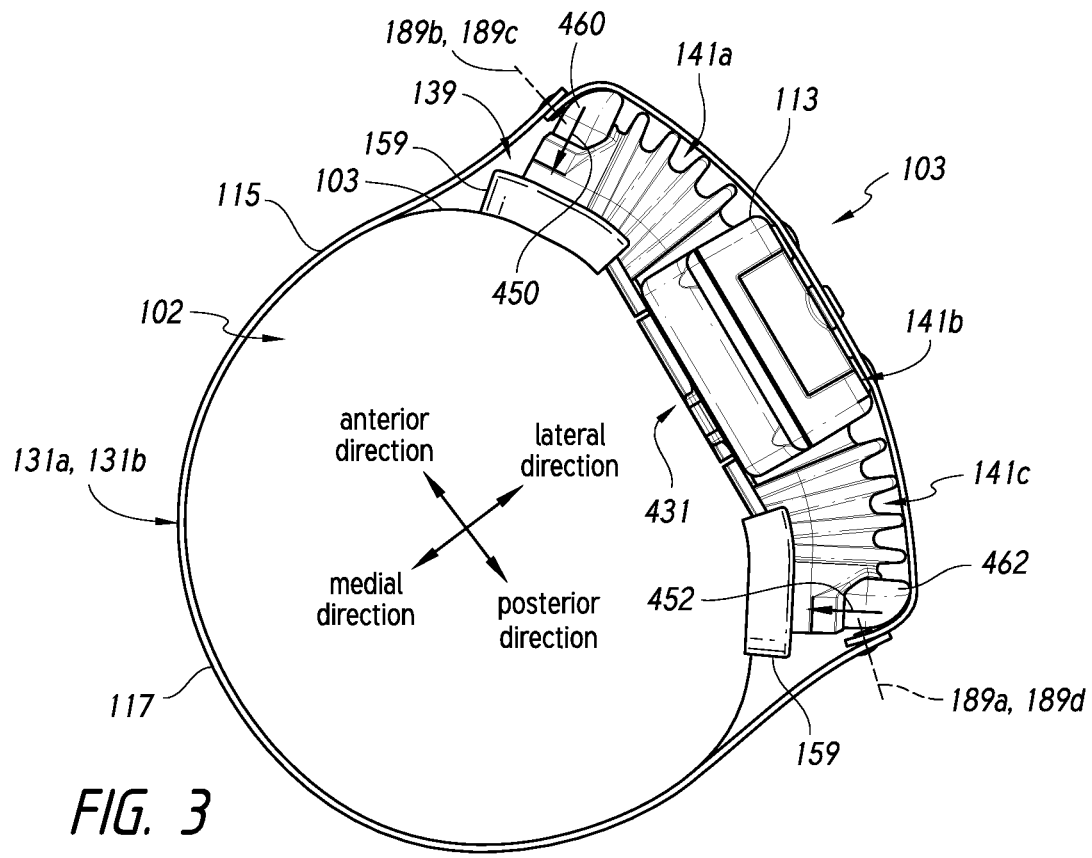
FIG. 3 is a view of an applicator system secured to a subject's thigh in accordance with embodiments of the technology.

The present disclosure describes treatment systems, conformable applicators, and methods for affecting targeted tissue. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the technology but are not described in detail. In some embodiments, a treatment system includes an applicator with three linked panels that provide comfortable surface application to a subject's body. One or more thermal elements (e.g., thermoelectric elements, fluid-cooled elements, etc.) can cool each panel. Straps and adhesive borders can cooperate to vacuumlessly hold the applicator during the procedure.

At least some embodiments of the present technology include treatment systems for affecting tissue in a target region of a human subject's body. The term "treatment system", as used generally herein, refers to cosmetic or medical treatment systems, as well as any treatment regimens or medical device usage. The treatment system can reduce or eliminate love handles, saddlebags, muffin tops, or other undesired body features associated with excessive tissue. In various embodiments, the treatment system includes a comfortable applicator with plurality of movable cooling units that are interconnected to provide a heat-exchanging surface (e.g., a generally continuous contact surface) for conductively heating/cooling targeted tissue. Each cooling unit can be configured to reduce a temperature of targeted tissue from a natural body temperature to a lower temperature. The applicator can overlay and conform to contoured treatment sites to effectively cool/heat the target region. A strap system can be used to minimize, reduce, or substantially eliminate movement of the applicator relative to the subject. In some embodiments, the strap system can hold the applicator in a non-planar configuration (e.g., a curved configuration, an arcuate configuration, etc.) to keep a desired number of cooling units (e.g., all or most of the cooling units) in thermal contact with the subject during therapy.

In some embodiments, a treatment system for non-invasive, transdermal removal of heat of a subject's body includes an applicator configured to conform to the subject's body and to selectively reduce a temperature of a target region beneath the epidermis of the subject. In one embodiment, the applicator can reduce the temperature of lipid-rich cells in the target region from a natural body temperature to a lower temperature in the target region. Cryoprotectant can lower a freezing point of non-targeted cells in or near the target region. The cryoprotectant, in some embodiments, protects non-lipid cells such that lipid-rich cells in the target region are substantially affected while non-lipid rich cells in the target region, or near the target region, are not substantially affected when the temperature is reduced.

At least some embodiments can include treatment systems having one or more conformable applicators for performing cryotherapy and a wearable applicator holder. In one embodiment, the applicator holder is a strap assembly that holds the applicator at a treatment site. The strap assembly can include straps that wrap about the subject to inhibit movement of the applicator. An applicator holder assembly can be adhered to the subject's skin to inhibit, limit, or substantially prevent movement of the applicator along the subject's skin. In some embodiments, the strap assembly can press the applicator against the subject such that the applicator conforms to the general shape (e.g., curvature) of the subject's body surface to which it is applied. The subject's tissue can conform to the applicator. The conformable applicator and the compliant tissue can cooperate to provide a high amount of thermal contact and to reduce, limit, or substantially eliminate gaps between the subject and the treatment system that would impair heat transfer.

At least some embodiments can include a treatment system having a conformable applicator and a strap assembly. The applicator's conformability to the subject's body can be determined, at least in part, by the strap assembly and one or more hinging features of the applicator. The strap assembly can cause the tissue to conform to the applicator, while the hinging features allow the applicator to conform to the region of the subject's body. The strap assembly can be used to adjust the distribution of pressure applied by the applicator. In some embodiments, the hinge features can include one or more spring assemblies to, for example, conform the applicator to a predetermined configuration. Additionally or alternatively, the hinge features can include one or more pins, joints, or the like.

In some embodiments, a treatment system for cooling a target region in a subject comprises a strap assembly and a conformable applicator including cooling units. The strap assembly can include one or more flexible straps coupled to one or more strap pivots. The flexible straps can rotatable about corresponding strap pivots to position the flexible straps at different locations along the subject to accommodate the subject's body while the cooling units are held in thermal contact with the subject's skin by the strap assembly wrapped around the subject. The conformable applicator can be a handheld applicator, a belt applicator, or other wearable applicator. In one embodiment, the treatment system can further include a cryoprotectant element. The cryoprotectant element can carry cryoprotectant and can be positionable between the applicator and the subject. In some embodiments, the cryoprotectant element can include an absorbent member (e.g., cotton pad, gauze, etc.) preloaded with cryoprotectant. Suitable exemplary cryoprotectants and processes for implementing cryoprotectants are described in commonly-assigned U.S. Patent Publication No. 2007/0255362 and U.S. patent application Ser. No. 14/610,807 entitled "COMPOSITIONS, TREATMENT SYSTEMS AND METHODS FOR IMPROVED COOLING OF LIPID-RICH TISSUE."

At least some embodiments of the present technology include a treatment system comprising a conformable applicator, a spring assembly, and a strap assembly. The conformable applicator can include first and second cooling units can be rotatable relative to each other to conform to the subject. The spring assembly interconnects the first and second cooling units so as to bias (e.g., pre-tension) the first and second cooling units into a predetermined configuration relative to one another and/or to resist twisting of the first and second cooling units relative to one another. The strap assembly can be configured to hold the conformable applicator in thermal contact with the subject's skin when the strap assembly is wrapped around the subject.

Some of the embodiments disclosed herein can be for cosmetically beneficial alterations of a variety of body regions. Some treatment procedures may be for the sole purpose of altering the body region to conform to a cosmetically desirable look, feel, size, shape or other desirable cosmetic characteristic or feature. Accordingly, at least some embodiments of the cosmetic procedures can be performed without providing an appreciable therapeutic effect (e.g., no therapeutic effect). For example, some treatment procedures may not include restoration of health, physical integrity, or the physical well-being of a subject. The cosmetic methods can target subcutaneous regions to change a subject's appearance such as, for example, procedures performed on a subject's saddlebags (i.e., excess adipose tissue at the subject's thighs and/or buttocks) and/or love handles (i.e., excess adipose tissue at the side of a subject's waistline). In other embodiments, however, the cosmetically desirable treatments may have therapeutic outcomes (whether intended or not), such as psychological benefits, alteration of body hormones levels (by the reduction of adipose tissue), etc.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, stages, or characteristics may be combined in any suitable manner in one or more examples of the technology. The headings provided herein are for convenience only and are not intended to limit or interpret the scope or meaning of the technology.

B. Cryotherapy

FIG. 1 and the following discussion provide a brief, general description of a treatment system 100 in accordance with some embodiments of the technology. The treatment system 100 can be a temperature-controlled system for exchanging heat from a subject 101. The treatment system 100 can include an applicator system 103 that conforms to highly contoured treatment sites to conductively cool a relatively large region of targeted tissue. The targeted tissue can be cooled without pulling or pinching tissue, thus enhancing comfort throughout therapy. The illustrated applicator system 103 is positioned to selectively cool subcutaneous, lipid-rich tissue of the subject's right thigh 102 to reduce or eliminate a saddlebag, although the applicator system 103 can wrap about other body parts to treat additional treatment sites.

Without being bound by theory, the selective effect of cooling is believed to result in, for example, membrane disruption, cell shrinkage, disabling, damaging, destroying, removing, killing or other methods of lipid-rich cell alteration. Such alteration is believed to stem from one or more mechanisms acting alone or in combination. It is thought that such mechanism(s) trigger an apoptotic cascade, which is believed to be the dominant form of lipid-rich cell death by non-invasive cooling. In any of these embodiments, the effect of tissue cooling is to selectively reduce lipid-rich cells by a desired mechanism of action, such as apoptosis, lipolysis, or the like. In some procedures, the applicator system 103 can cool the skin of the patient to a temperature in a range of from about −20° C. to about 20° C. In other embodiments, the cooling temperatures can be from about −20° C. to about 10° C., from about −18° C. to about 5° C., from about −15° C. to about 5° C., or from about −15° C. to about 0° C. In further embodiments, the cooling temperatures can be equal to or less than −5° C., −10° C., −15° C., or in yet another embodiment, from about −15° C. to about −25° C. Other cooling temperatures can be used.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" Cryobiology 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption or dysfunction, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" Heart Failure Reviews, 8, 277-284 (2003). Other possible mechanisms of adipocyte damage, described in U.S. Pat. No. 8,192,474, relate to ischemia/reperfusion injury that may occur under certain conditions when such cells are cooled as described herein. For instance, during treatment by cooling as described herein, the targeted adipose tissue may experience a restriction in blood supply and thus be starved of oxygen due to isolation as a result of applied pressure, cooling which may affect vasoconstriction in the cooled tissue, or the like. In addition to the ischemic damage caused by oxygen starvation and the buildup of metabolic waste products in the tissue during the period of restricted blood flow, restoration of blood flow after cooling treatment may additionally produce reperfusion injury to the adipocytes due to inflammation and oxidative damage that is known to occur when oxygenated blood is restored to tissue that has undergone a period of ischemia. This type of injury may be accelerated by exposing the adipocytes to an energy source (via, e.g., thermal, electrical, chemical, mechanical, acoustic, or other means) or otherwise increasing the blood flow rate in connection with or after cooling treatment as described herein. Increasing vasoconstriction in such adipose tissue by, e.g., various mechanical means (e.g., application of pressure or massage), chemical means or certain cooling conditions, as well as the local introduction of oxygen radical-forming compounds to stimulate inflammation and/or leukocyte activity in adipose tissue may also contribute to accelerating injury to such cells. Other yet-to-be understood mechanisms of injury may exist.

In addition to the apoptotic mechanisms involved in lipid-rich cell death, local cold exposure is also believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" Aviation, Space and Environmental Medicine 70, 42-50 (1999).

One expected advantage of the foregoing techniques is that the subcutaneous lipid-rich cells in the target region can be reduced generally without collateral damage to non-lipid-rich cells in the same region. In general, lipid-rich cells can be affected at low temperatures that do not affect non-lipid-rich cells. As a result, lipid-rich cells, such as those associated with cellulite, saddlebags, love handles, muffin tops, etc., can be affected while other cells in the same region are generally not damaged even though the non-lipid-rich cells at the surface (e.g., cells in the dermis and/or epidermis) may be subjected to even lower temperatures than those to which the lipid-rich cells are exposed.

In a typical procedure, the applicator system 103 can remove heat from the underlying tissue through the upper layers of the skin and create a thermal gradient with the coldest temperatures near the cooling surface of the applicator system 103 (i.e., the temperature of the upper layer(s) of the skin can be lower than that of the targeted underlying cells). It may be challenging to reduce the temperature of the deep cells (e.g., lipid-rich cells) low enough to be destructive to these target cells (e.g., induce apoptosis, cell death, etc.) while also maintaining the temperature of the upper and surface skin cells high enough so as to be protective (e.g., non-destructive). The temperature difference between these two thresholds can be small (e.g., approximately, 5° C. to about 10° C., less than 10° C., less than 150° C., etc.). Protection of the overlying cells (e.g., typically water-rich dermal and epidermal skin cells) from freeze damage during dermatological and related aesthetic procedures that require sustained exposure to cold temperatures may include improving the freeze tolerance and/or freeze avoidance of these skin cells. Cryoprotectants can be used to inhibit or prevent such freeze damage.

Applicators can be used to perform a wide range of different cryotherapy procedures that involve, for example, at least partially or totally freezing tissue to form crystals that alter targeted cells to cause skin tightening, skin thickening, or fibrosis; reduce glands, or affect other targeted cells. To avoid destroying skin cells, the surface of the patient's skin can be cooled to temperatures no lower than, for example, −50° C., −40° C., −30° C., −20° C., or −10° C. for a duration short enough to avoid, for example, excessive ice formation, permanent thermal damage, or significant hyperpigmentation or hypopigmentation (including long-lasting or permanent hyperpigmentation or hypopigmentation). In another embodiment, destruction of skin cells can be avoided by applying heat to the surface of the patient's skin to heat the skin cells, in particular the epidermal cells, above their freezing temperature. The patient's skin can be warmed to at least about −30° C., −25° C., −20° C., −15° C., −10° C., 0° C., 10° C., 20° C., 30° C., or other temperature sufficient to avoid, for example, excessive ice formation, permanent thermal damage, or significant hyperpigmentation or hypopigmentation of the non-targeted and/or epidermal tissue. In some treatments, skin can be cooled to produce partial freeze events that cause apoptotic damage to skin tissue without causing significant damage to adjacent subcutaneous tissue. Other cryotherapy procedures may cause non-apoptotic responses.

C. Treatment Systems

FIG. 1 shows the treatment system 100 that includes the applicator system 103, a connector 104, and a control module 106. The connector 104 can provide energy (e.g., electrical energy) and fluid (e.g., coolant) from the control module 106 to the applicator system 103. The applicator system 103 is positioned along the subject's leg 90 and can include a conformable applicator 113 ("applicator 113") and a strap assembly 115. The applicator 113 can conform to the leg 90 to provide high thermal conductivity. The strap assembly 115 can include flexible straps 117a-d (collectively "straps 117") that can be positioned to comfortably hold the applicator 113. In some procedures, the subject's hip bone can be positioned between the straps 117 to help anchor the applicator 113. The straps 117a-d can be rotated about strap axes of rotation 189a-d, respectively, to provide a desired fit and desired distribution of pressure applied by the applicator 113. The straps 117a-d can cause the tissue to conform to the applicator 113, while conformability of the applicator 113 allows the applicator 113 to assume the general shape of the body surface to which it is applied. The applicator 113 can be a non-vacuum based cooling device capable of cooling subcutaneous tissue without pinching, thus allowing treatment of generally non-pinchable regions, such as non-pinchable fat bulges (e.g., saddlebags), abdominal regions, flank regions, etc.

FIG. 2 is a cross-sectional view of the connector 104 in accordance with at least some embodiments of the technology. The connector 104 can include a main body 179, a supply fluid line or lumen 180a ("supply fluid line 180a"), and a return fluid line or lumen 180b ("return fluid line 180b"). The main body 179 may be configured (via one or more adjustable joints) to "set" in place for the treatment of the subject 101 and can include a multi-lumen hose, a covering, a sheath, or other components for protecting electrical/fluidic lines. The supply and return fluid lines 180a, 180b can be conduits comprising, in whole or in part, polyethylene, polyvinyl chloride, polyurethane, and/or other materials that can accommodate circulating coolant, such as water, glycol, synthetic heat transfer fluid, oil, a refrigerant, and/or any other suitable heat conducting fluid. In one embodiment, each fluid line 180a, 180b can be a flexible hose surrounded by the main body 179. The connector 104 can also include one or more electrical lines 112 (one illustrated schematically in FIG. 2) for providing power to the applicator 113 and a control line 116 (one illustrated schematically in FIG. 2) for providing communication between the control module 106 (FIG. 1) and the applicator 113 (FIG. 1). In various embodiments, the connector 104 can include a bundle of fluid conduits, a bundle of power lines, wired connections, and other bundled and/or unbundled components. The configuration of the connector 104 can be selected to provide ergonomic comfort, minimize unwanted motion (and thus potential inefficient removal of heat from the subject 101), and/or to provide an aesthetic appearance to the treatment system 100.

Referring again to FIG. 1, the control module 106 can include a fluid chamber 105 (illustrated in phantom line), a power supply 110 (illustrated in phantom line), and a controller 114 carried by a housing 124 with wheels 126. The control module 106 can include a refrigeration unit, a cooling tower, a thermoelectric chiller, heaters, or any other device capable of controlling the temperature of coolant in the fluid chamber 105. The coolant can be continuously or intermittently delivered to the applicator 113 via the supply fluid line 180a (FIG. 2) and can circulate through the applicator 113 to absorb heat. The coolant, which has absorbed heat, can flow from the applicator 113 back to the control module 106 via the return fluid line 180b (FIG. 2). For warming periods, the control module 106 can heat the coolant such that warm coolant is circulated through the applicator 113. Alternatively, a municipal water supply (e.g., tap water) can be used in place of or in conjunction with the control module 106.

An operator can control operation of the treatment system 100 using an input/output device 118 of the controller 114. The power supply 110 can provide a direct current voltage for powering electrical elements of the applicator 113 via the line 112 (FIG. 2). The controller 114 can monitor process parameters based on output from sensors (e.g., sensors placed proximate to the applicator 113, sensors of the applicator 113, etc.) communicated via the control line 116 (FIG. 2). In some embodiments, the controller 114 can exchange data with the applicator 113 via a wireless or an optical communication link. The controller 114 can monitor and adjust treatment based on one or more treatment profiles and/or patient-specific treatment plans, such as those described, for example, in commonly assigned U.S. Pat. No. 8,275,442. Each custom treatment profile can include one or more segments, and each segment can include a specified duration, a target profile, or the like. For example, a treatment profile for reducing love-handles or saddlebags can include specified treatment sites, specified durations for each treatment site, and/or target temperature profiles for each treatment site. In some cryotherapy sessions, saddlebags located on opposite sides of a subject's body are treated in the same session using the same applicator or multiple applicators. Additionally, a treatment profile can include specific temperature profiles for each cooling unit of the applicator. Exemplary individually controlled heat-exchanging cooling units are described herein and additional applicators and cooling units are described in commonly assigned U.S. Patent Publication Nos. 2008/0077211 and 2011/0238051.

D. Applicator Systems

FIG. 3 is a view of the applicator system 103 secured to the subject's thigh 102 in accordance with embodiments of the technology. The strap assembly 115 in a closed configuration can keep the applicator 113 between two borders 159 of a multi-piece holder assembly 139. The sizes of loops 131a, 131b formed by the straps 117 can be adjusted to provide a patient-specific fit. The applicator 113 can include cooling units 141a-c (collectively "cooling units 141") rotatably coupled together. The borders 159 are coupled to the subject's skin (e.g., via adhesive) and are spaced apart from one another to hold the cooling units 141a, 141c. During treatment, the strap assembly 115 and borders 159 can cooperate to keep the applicator 113 at the treatment site even if the subject moves his/her thigh 102. If the treatment segment is relatively long (e.g., longer than 20 minutes), the subject may want to periodically move his/her leg 90. In some treatments, the applicator 113 can be kept stationary relative to the thigh 102 during the entire session. In other treatments, the strap assembly 115 and borders 159 can be moved to position the applicator 113 at multiple treatments sites.

Figure 4:
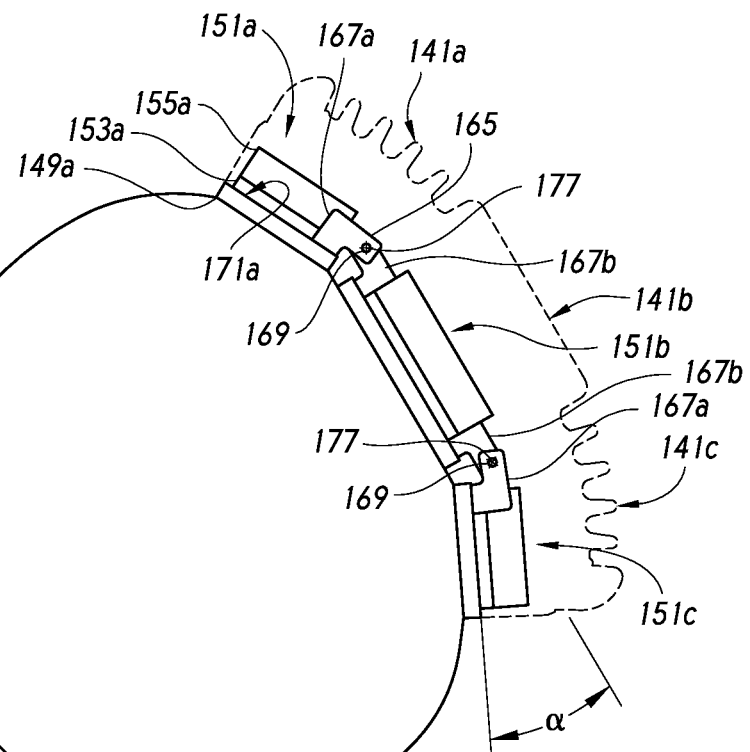
FIG. 4 is a view of a conformable applicator suitable for use with the applicator system of FIG. 3 in accordance with embodiments of the technology.

FIG. 4 is a view of internal components of the applicator 113. The cooling units 141a-c can include heat-exchanging units 151a-c, respectively, configured to extract heat from the subject. A pivot mechanism in the form of a hinge 165 rotatably couples together the cooling units 141a, 141b. Another pivot mechanism in the form of a hinge 165 rotatably couples together the cooling units 141b, 141c. The description of one of the cooling units 141a-c applies to the others, except as indicated otherwise.

The heat-exchanging unit 151a can include a heat-exchanging element 149a, a thermoelectric device 153a, and a fluid-cooled device 155a. The heat-exchanging element 149a can include a plate and a covering. The plate can be flat or shaped (e.g., curved) and can be made of metal or other conductive material (e.g., a rigid conductive material, a flexible conductive material, etc.), and the covering can be a film, a sheet, a sleeve, or other component suitable for defining an interface surface. In one embodiment, the covering can be positioned between the plate and the subject's skin. In other embodiments, an exposed surface of the plate can define the exposed surface of the applicator 113. The thermoelectric device 153a can include one or more thermoelectric elements for cooling the heat-exchanging element 149a. The fluid-cooled device 155a can exchange heat with the backside of the thermoelectric device 153a to keep the thermoelectric device 153a at or below target temperature. The heat-exchanging unit 151a can have other configurations for providing desired heat transfer capabilities.

Each hinge 165 can include brackets 167a, 167b and a pin 169. The bracket 167a can be fixedly coupled to a backside 171a of the heat-exchanging element 149a. Each pin 169 defines an axes of rotation 177 (see FIGS. 5 and 6) about which the cooling unit 141a, 141c, respectively, can rotate an angle of rotation α (one angle of rotation α is identified for cooling unit 141c of FIG. 4) that can be equal to or less than about 10 degrees, 20 degrees, 30 degrees, 40 degrees, or other desired degrees of rotation. In the illustrated embodiment, angle of rotation α can be about 30 degrees (e.g., 30 degrees±3 degrees) to provide sufficient rotation for conforming to outer thigh curvatures. Referring to FIGS. 3 and 4, the axes of rotation 177 can be non-parallel to the strap axes of rotation 189a-c (FIG. 3). In some embodiments, the axes of rotation 177 extend in a direction generally perpendicular to the direction of the axes of rotation 189a-d. As such, the loops 131a, 131b formed by the straps 117 can be moved in opposite directions (e.g., superior and inferior directions along a body part) while the cooling units 141 can be moved radially inward/outward relative to the body part.

Figure 5:
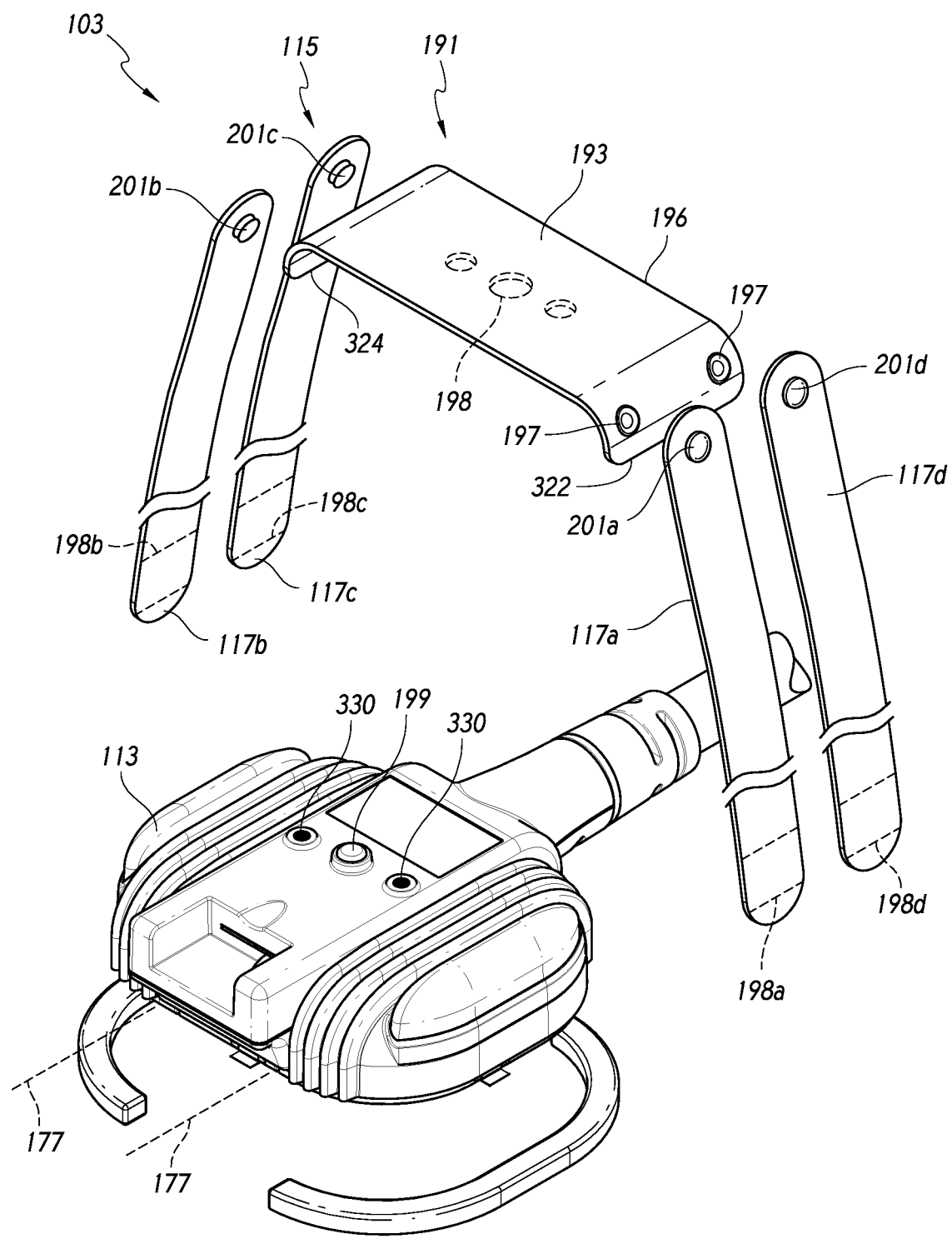
FIG. 5 is an exploded isometric view of an applicator system suitable for use with the treatment system of FIG. 1 in accordance with embodiments of the technology.

FIG. 5 is an exploded isometric view of the applicator system 103 that includes a retainer apparatus 191 with a strap holder 193 ("holder 193") and the strap assembly 115. The holder 193 is configured to releasably coupled to the applicator 113 and can have a rigid or flexible main body 196 and strap pivot features 197 (two identified) for connecting to respective straps 117. The main body 196 can be made, in whole or in part, of leather, fabric, plastic (e.g., rigid plastic, flexible plastic, etc.), and/or other suitable material for applying forces to the applicator 113. The strap pivot features 197 ("strap pivots 197") can be snaps, holes, pins, or other features for rotatably coupling to the straps 117. The holder 193 can have an aperture or recess 198 for receiving an alignment feature 199 (e.g., a boss) to keep the holder 193 relatively centered over the applicator 113 for uniform pressure distribution.

Each strap 117a-d can include a corresponding coupling feature 201a-d for releasably coupling to the strap pivot features 197. In one embodiment, the coupling features 201a-d and strap pivots 197 form snaps. The straps 117a-c can have fixed or adjustable lengths and can include one or more couplers 198a-c (illustrated in dashed line), such as (e.g., hook and loop type fastener), snaps, buckles, or the like. Additionally, the straps can be coupled together to define loops (e.g., loops 131a, 131b shown in FIG. 3), and the sizes of the loops can be increased or decreased to decrease or increase the pressure applied by the applicator 113 to the subject. The dimensions (e.g., lengths, widths, etc.) of the straps 117 can be selected based on the planned treatment sites. In some embodiments, each strap 117 has a length in a range of about 30 inches (76 cm) to about 36 inches (91 cm) and a width in a range of about 1.5 inches (3.8 cm) to about 2.5 inches (6.4 cm). The straps 117 can be made, in whole or in part, of a flexible material, such as leather, fabric, plastic, or other drapable material. In some embodiments, each strap 117 is a leather or plastic belt.

Figure 6:
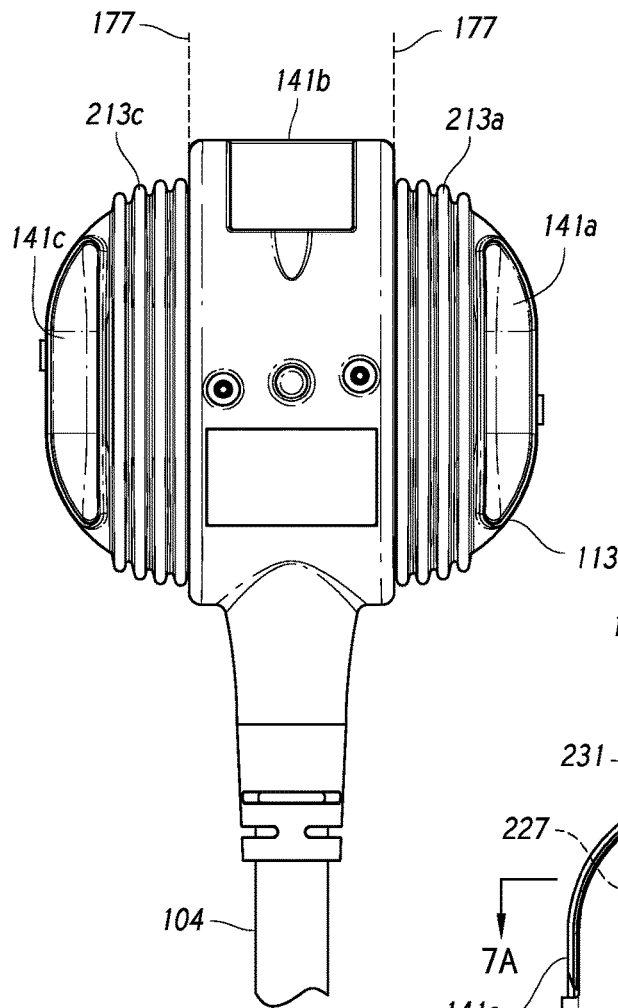
FIG. 6 is a top plan view of a conformable applicator in accordance with embodiments of the technology.
Figure 7:
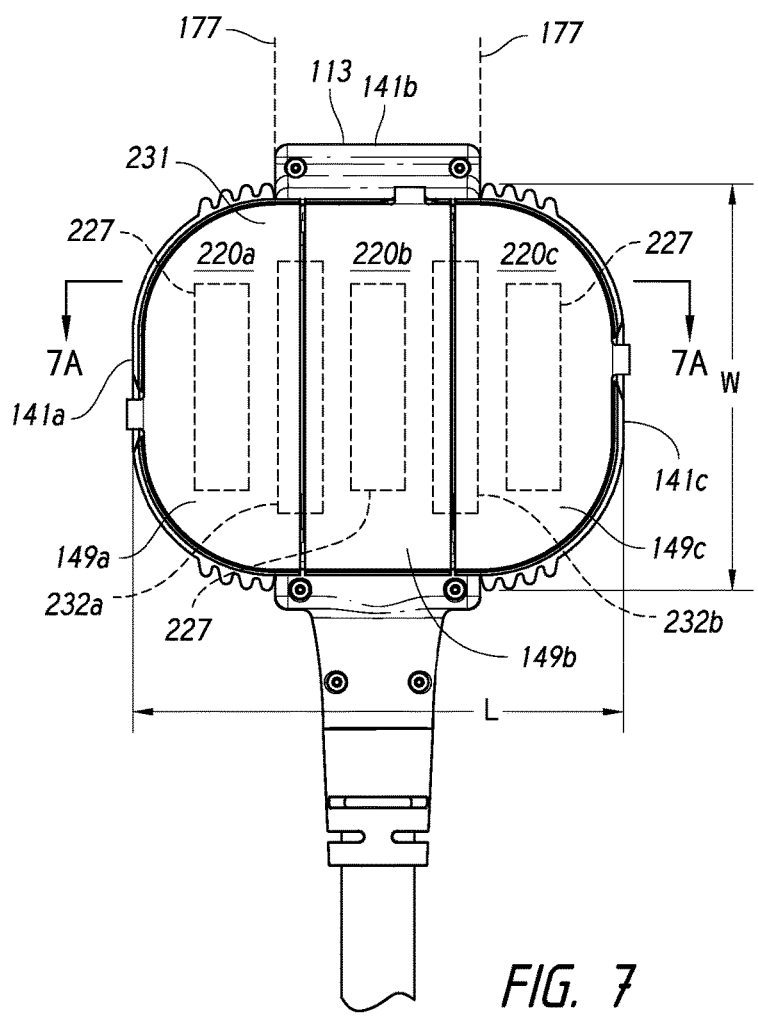
FIG. 7 is a bottom view of the conformable applicator of FIG. 6 in accordance with embodiments of the technology.

FIG. 6 is a top plan view of the applicator 113 in accordance with embodiments of the technology. FIG. 7 is a bottom view of the applicator 113 of FIG. 6. Referring now to FIG. 6, the cooling unit 141b can be a central or main cooling unit that distributes power and fluid to the side cooling units 141a, 141c. The cooling units 141a, 141c can include covers 213a, 213c, illustrated as flexible bellow covers, that expand and contract to allow rotation of the cooling units 141a, 141c about the axes of rotation 177. Referring now to FIG. 7, the heat-exchanging elements 149a-c (collectively "heat-exchanging elements 149") can define a generally continuous heat-exchanging surface 231 having a width W of about 5 inches to about 6 inches and a length L of about 7 inches (18 cm) to about 8 inches (20 cm). In one embodiment, the width is about 5.5 inches (14 cm) and the length is about 7 inches (18 cm). The area of the heat-exchanging surface 231 can be in a range of about 30 in$^2$ (194 cm$^2$) to about 45 in$^2$ (290 cm$^2$). Other dimensions and areas can be selected based on the size of the patient and treatment sites.

The applicator 113 can include one or more sensors 227 (illustrated in phantom line) that measure, e.g., an interface temperature, heat flux across a surface of or plane within respective interface layers 220a-c (e.g., a cover/film of the heat-exchanging elements 149a-c), and/or pressure (e.g., contact pressure) with the patient's skin. The sensors 227 can be coupled to the surface of the interface layers 220, embedded in the interface layers 220, or at other suitable locations. Additional sensors may be included for measuring tissue impedance, treatment application force, tissue contact with the applicator and energy interaction with the skin of the patient among other process parameters. In one embodiment, feedback data associated heat removal from tissue (e.g., non-targeted tissue, targeted tissue, etc.) can be collected in real-time. Real-time collection and processing of such feedback data can be used in concert with treatment administration to ensure that the process parameters used to alter or reduce subcutaneous adipose tissue are administered correctly and efficaciously. The sensor measurements can indicate other changes or anomalies that can occur during treatment administration. For example, an increase in temperature detected by a heat flux sensor can indicate a freezing event at the skin or underlying tissue (i.e., dermal tissue). An increase in temperature as detected by the heat flux sensors can also indicate movement associated with the applicator 113, causing the applicator 113 to contact a warmer area of the skin, for example. Methods and systems for collection of feedback data and monitoring of temperature measurements are described in commonly assigned U.S. Pat. No. 8,285,390.

Figure 7A:
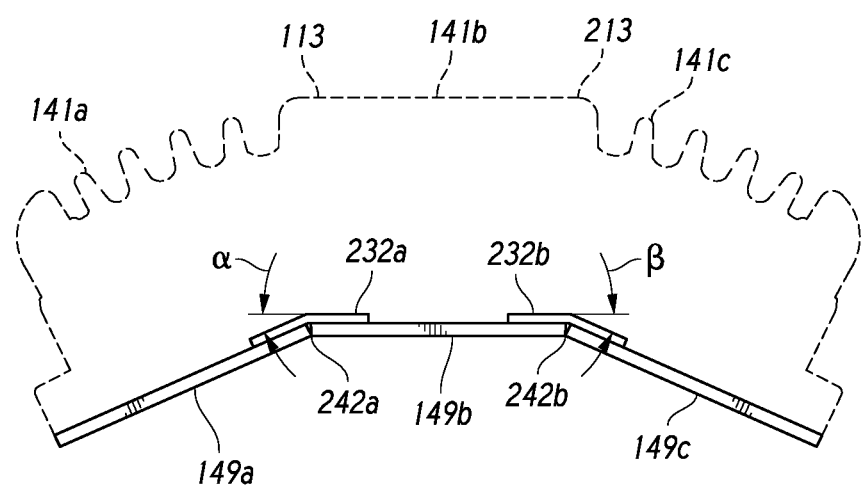
FIG. 7A is a cross-sectional view of the conformable applicator taken along line 7A-7A of FIG. 7.

FIG. 7 shows pre-loaded spring assemblies 232a, 232b (collectively "spring assemblies 232"). FIG. 7A is a cross-sectional view of the applicator 113 with the spring assembly 232a connecting the cooling units 141a, 141b and the spring assembly 232b connecting the cooling units 141b, 141c. The spring assemblies 232 cooperate to position the cooling units 141 at predetermined bend angles relative to one another and can overcome the inherent stiffness of the cover 213 (shown in phantom line) for biasing the assembly 113 to a treatment configuration for reducing or limiting the amount of tensioning in the straps 117 needed to hold the applicator 113 against the subject. By holding the applicator 113 in a configuration generally corresponding to the treatment site, over-tensioning of the straps 117 can be avoided. Over-tensioning of the straps 117 may cause adjacent cooling units 141 to bend too much relative to one another which may cause at least a portion of the cooling units 141 to lift off the patient. The spring assemblies 232 can provide sufficient biasing forces to pre-bend the applicator 113 to prevent such over-tensioning of the straps, reduce or prevent lift off of the cooling units 141, or otherwise enhance performance. In addition, a longitudinal stiffness of the spring assemblies 232 resists twisting of the cooling units 141 relative to one another whereby, by reference to FIG. 7, a top portion of any of the heat exchanging elements 141a-c may otherwise want to rotate or bend into a plane of FIG. 7 more or less so than a bottom portion of the respective heat exchange elements in response to forces imposed by the strap assembly 115. Without the spring assemblies, it is only the hinges that can resist such twisting, and hinges may be ineffective in solely being able to resist significant twisting.

Referring to FIG. 7A, the spring assembly 232a can be coupled to the backsides of the heat-exchanging elements 149a, 149b and can extend across a seam or gap 242a. The spring assembly 232b can be coupled to the backsides of the heat-exchanging elements 149b, 149c and can extend across a seam or gap 242b. In some embodiments, the spring assemblies 232 can be coupled to the heat-exchanging elements 149 by one or more fasteners or welds. In other embodiments, the spring assemblies 232 are incorporated into or part of the heat-exchanging elements 149.

The spring assemblies 232 can bias the applicator 113 to an optimum configuration with, for example, optimum bend angles $\alpha$, $\beta$ between about 5 degrees and about 60 degrees, between about 10 degrees and about 50 degrees, between about 20 degrees and about 40 degrees, or other suitable angles. To treat thighs, the bend angles $\alpha$, $\beta$ can be between about 25 degrees and about 35 degrees. In some embodiments, the bend angles $\alpha$, $\beta$ are about 30 degrees. To treat arms, the bend angles $\alpha$, $\beta$ can be equal to or greater than about 30 degrees, 40 degrees, 50 degrees, or 60 degrees. To treat a patient's abdomen or love handles, the bend angles $\alpha$, $\beta$ can be equal to or less than about 30 degrees, 20 degrees, 10 degrees, or 5 degrees.

The spring assemblies 232 can be made of metal (e.g., spring steel, resilient metal, etc.), plastic, or other material with desired mechanical properties to urge the applicator 113 to a desired bend configuration. In some embodiments, each spring assembly 232 includes spring steel that is preloaded (e.g., bent, pre-shaped, etc.) to provide pre-tensioning for an optimum configuration selected based on, for example, the treatment site, pressure to be applied to the treatment site, etc. Other types of spring assemblies can be used and can include, without limitation, one or more helical springs, extension springs, or coil springs and can be made, in whole or in part, of metal (e.g., spring steel, aluminum, etc.), plastic, or other material with desired mechanical properties. The applicators discussed in connection with FIGS. 18-23 can also have spring assemblies discussed herein. The number and configuration of the spring assemblies can be selected based on the desired configuration, number of cooling units, and characteristics of components of the applicator.

Figure 8:
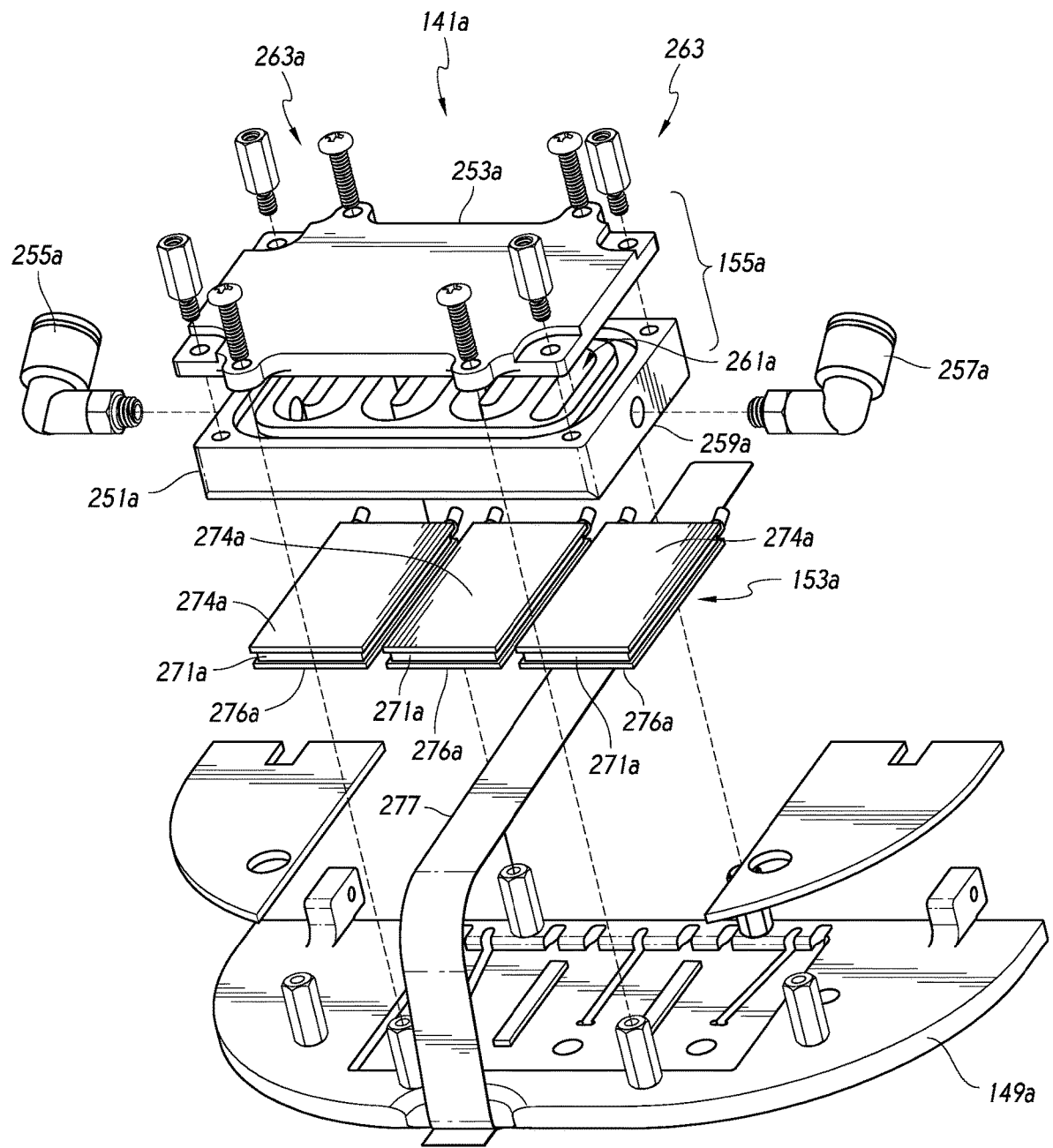
FIGS. 8 and 9 are exploded isometric views of cooling units in accordance with embodiments of the technology.

FIG. 8 is an exploded isometric view of components of the cooling unit 141a in accordance with embodiments of the technology. The fluid-cooled device 155a can include a fluid circulation element 251a, a cover 253a, and inlet and outlet ports 255a, 257a. The fluid circulation element 251a can include a main body 259a that defines a fluid chamber 261a, illustrated with a serpentine shape. The cover 253a can be coupled to the main body 259a by fasteners 263a to close the chamber 261a. Coolant can flow through the inlet port 255a into the chamber 261a, circulate through the chamber 261a to absorb heat from the thermoelectric device 153a, and can exit the chamber 261a via the outlet port 257a. The heated coolant can flow back to the control module.

Figure 9:
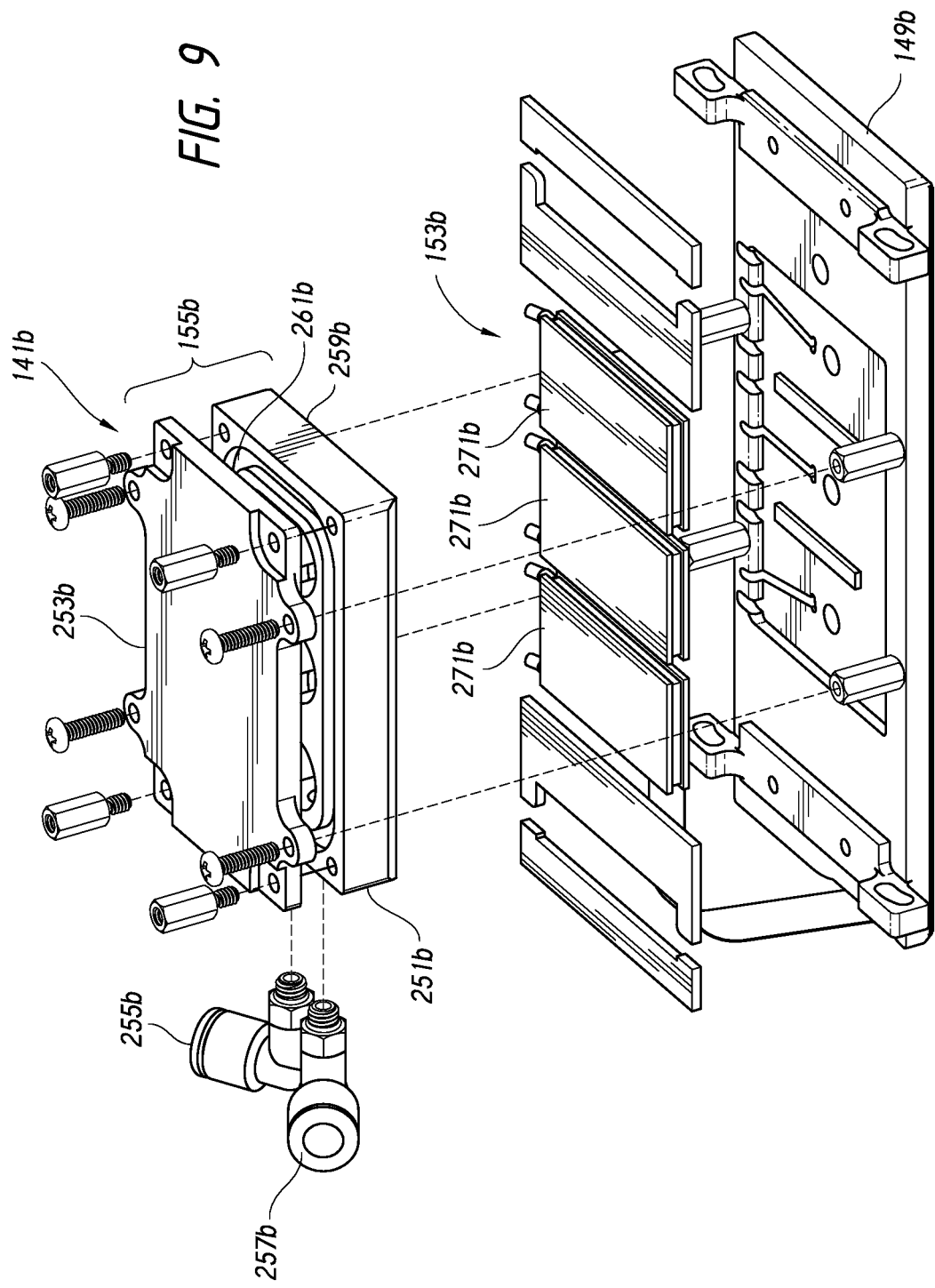

FIG. 9 is an exploded view of the cooling unit 141b in accordance with embodiments of the technology. The fluid-cooled device 155b includes a fluid-cooled element 251b, a cover 253b, and inlet and outlet ports 255b, 257b. The fluid-cooled element 251b includes a main body 259b and a fluid chamber 261b. The thermoelectric device 153b includes an array of thermoelectric elements 271b sandwiched between the fluid-cooled device 155b and the heat-exchanging element 149b. Although the illustrated embodiment has three rectangular thermoelectric elements 271b, the thermoelectric device 153b can include a greater or lesser number of thermoelectric elements with other shapes.

Figure 10:
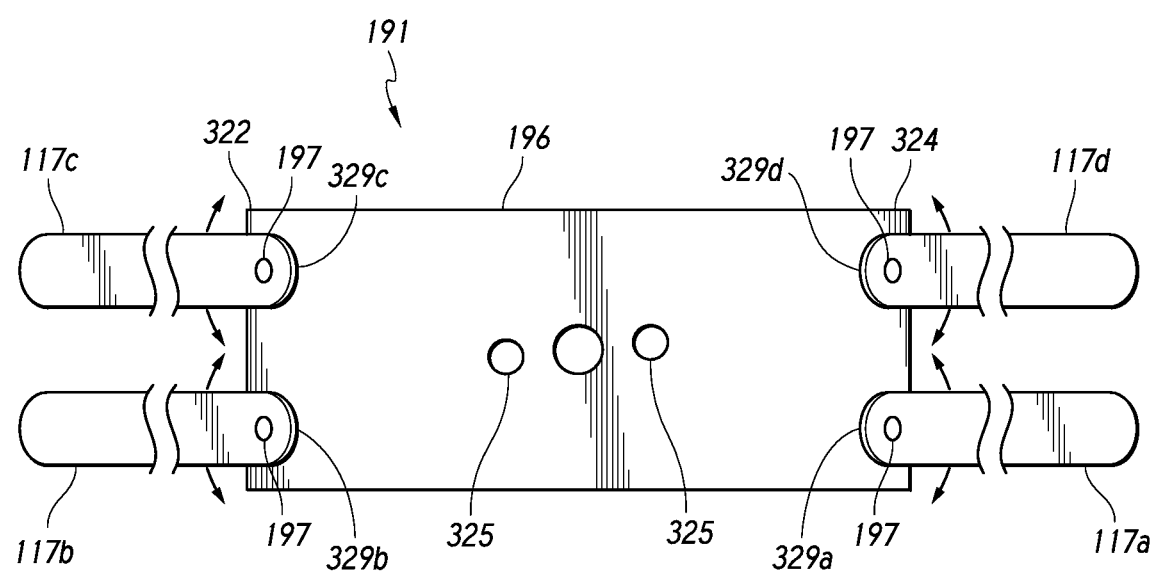
FIG. 10 is a top plan view of a strap system in accordance with embodiments of the technology.

FIG. 10 is a top plan view of the applicator retainer apparatus 191 in accordance with embodiments of the technology. The main body 196 has a first end 322 with two strap pivots 197 and an opposing second end 324 with two strap pivots 197. The strap pivots 197 at the end 322 can be spaced apart a sufficient distance to help distribute forces across the cooling unit 141a (FIG. 5), and the strap pivots 197 at the end 324 can be spaced apart a sufficient distance to help distribute forces to the cooling unit 141c (FIG. 5). The forces applied by the straps 117 can help keep most or all of the cooling units 141 in thermal contact with the subject. The main body 196 can include coupler features 325 (e.g., snaps, magnets, etc.) coupleable to respective couplers 330 (FIG. 5) of the applicator 113. When the main body 196 is coupled to the cooling unit 141b, the cooling units 141a, 141c can be rotated toward the subject by the tensioned main body 196. Ends 329a-d of the straps 117a-d, respectively, can be translationally fixed to the main body 196. In one embodiment, each strap pivot 197 can define one degree of freedom, such as one rotational degree of freedom, as indicated by arrows in FIG. 10.

Figure 11:
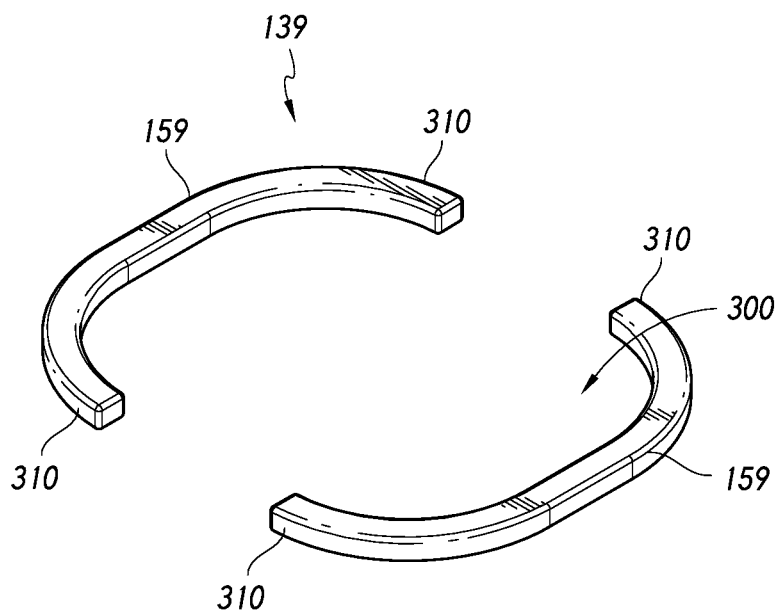
FIG. 11 is an isometric view of a multi-piece applicator holder assembly in accordance with embodiments of the technology.
Figure 12:
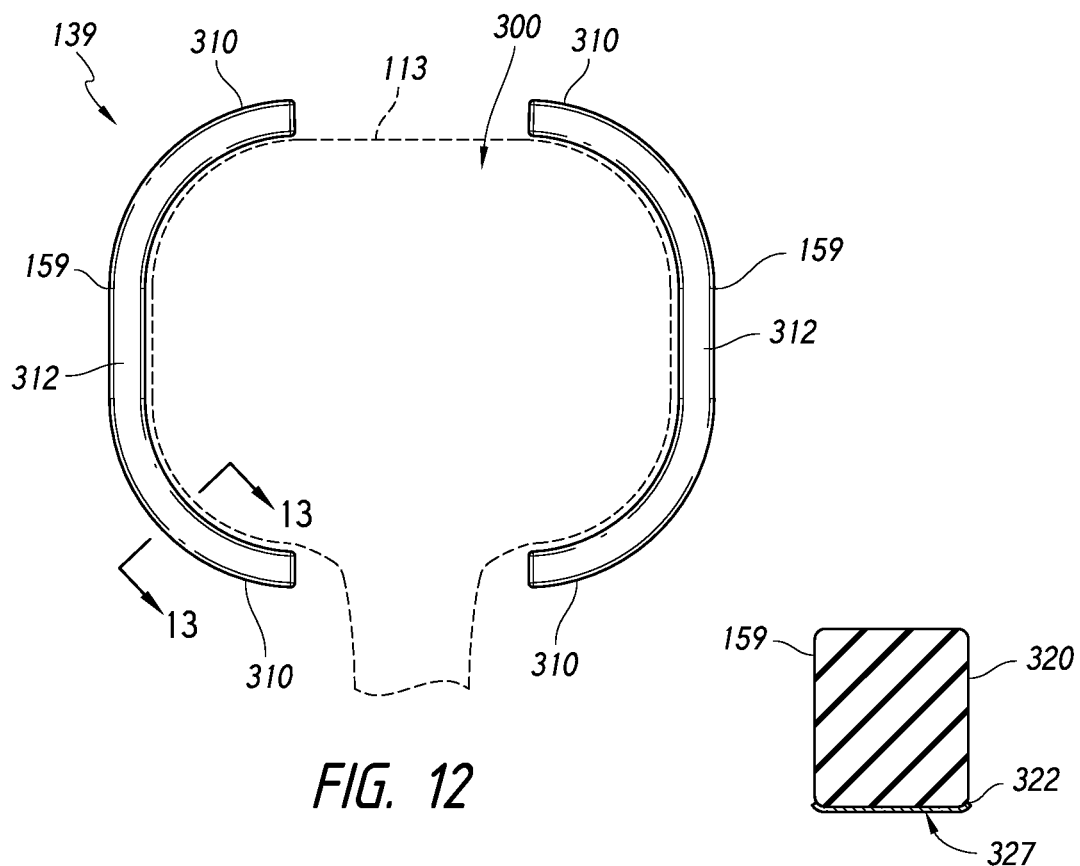
FIG. 12 is a top plan view of the holder assembly of FIG. 11.

FIG. 11 is an isometric view of the holder assembly 139 in accordance with embodiments of the technology. FIG. 12 is a top plan view of the holder assembly 139 of FIG. 11. When the borders 159 are located on the subject, the applicator can be located in an applicator-receiving opening 300. As shown in FIG. 12, the applicator-receiving opening 300 can have a shape that is complementary to the shape of the applicator 113 (shown in phantom line). The borders 159 can be sufficiently compliant to conform to highly contoured regions of the subject's body and can be made, in whole or in part, of foam (e.g., closed-cell foam, open-cell foam, etc.), rubber, polymers, or other materials suitable for contacting the applicator without damaging the applicator and/or causing patient discomfort. Referring now to FIG. 12, each border 159 can include a pair of arms or end portions 310 ("end portions 310") and a main body 312. The end portions 310 can be arcuate and can be positioned on opposite sides of the applicator 113. The main bodies 312 can be configured to contact opposite ends of the applicator 113.

Figure 13:
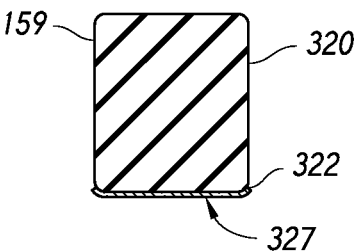
FIG. 13 is a cross-sectional view of the holder assembly taken along line 13-13 of FIG. 12 in accordance with embodiments of the technology.

FIG. 13 is a cross-sectional view of one border 159 taken along line 13-13 of FIG. 12. The border 159 has a substantially rectangular cross section and a main body 320 and adhesive 322, which defines a patient-contact surface 327. The adhesive 322 can be configured to releasably couple to the subject's skin and can comprise pressure-sensitive adhesive or other adhesive (e.g., medical-grade adhesive). The composition of the borders 159 can be selected based on the desired adhesion strength, mechanical characteristics (e.g., compliance, cushioning, or other characteristics). In various embodiments, the border 159 can have other polygonal cross sections (e.g., square cross sections), rounded polygonal cross sections, or other suitable configurations for engaging an applicator.

FIGS. 14-17 illustrate stages of a cryotherapy procedure performed on a subject 101 in accordance with embodiments of the technology. Generally, the borders 159 are adhered to the subject's skin such that they cooperate to at least partially surround a treatment site. The applicator 113 can be placed in thermal contact with the subject's skin and can extract heat from a subcutaneous target region while the strap assembly 115 and borders 159 cooperate to minimize, limit, or substantially eliminate movement of the applicator 113 relative to the treatment site. The borders 159 can be repositioned to treat additional treatment sites. Various details of cryotherapy procedures are discussed in detail below.

The subject's skin can be cleaned using alcohol or other suitable skin cleaner. Liners can cover adhesive surfaces of the borders 159 and can be paper liners, plastic release liners, or other types of liners. The liners can be conveniently removed from the borders 159 to expose the adhesive patient-contact surface 327 (FIG. 13). The borders 159 can be adhered to the subject 101 before, during, or after the placement of the applicator 113 at a treatment site. The configurations, dimensions, and number of borders can be selected based on, for example, the location and dimensions of the treatment site, the configuration of the applicator, or other treatment parameters. Additional applicator holder assemblies and borders are discussed in connection with FIGS. 18-23.

Figure 14:
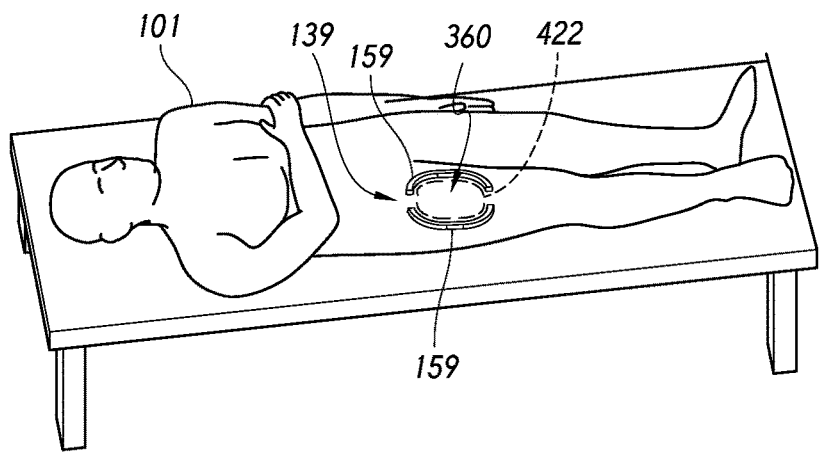
FIGS. 14-17 are a series of views of a method of performing cryotherapy in accordance with various embodiments of the present technology.

FIG. 14 is an isometric view of the borders 159 mounted on the subject 101 to partially surround a treatment site 360. The borders 159 can also help contain flowable cryoprotectant. Adhesive of the borders 159 can adhere to the subject's skin to prevent cryoprotectant from leaking or spreading to areas of the skin adjacent to but outside of the treatment site 360. A cryoprotectant element 422 (illustrated in phantom line) can have a configuration that generally matches the configuration of the applicator 113. In one embodiment, the cryoprotectant element 422 can comprise cotton and/or gauze material that has absorbed or otherwise carries or contains cryoprotectant. In one embodiment, the cryoprotectant element 422 is a cotton pad preloaded with cryoprotectant comprising a flowable freezing point depressant. The borders 159 can be positioned at opposite sides of the cryoprotectant element 422 to limit or substantially prevent movement of the cryoprotectant element 422. For example, the borders 159 may closely surround and hold the cryoprotectant element 422.

Figure 15:
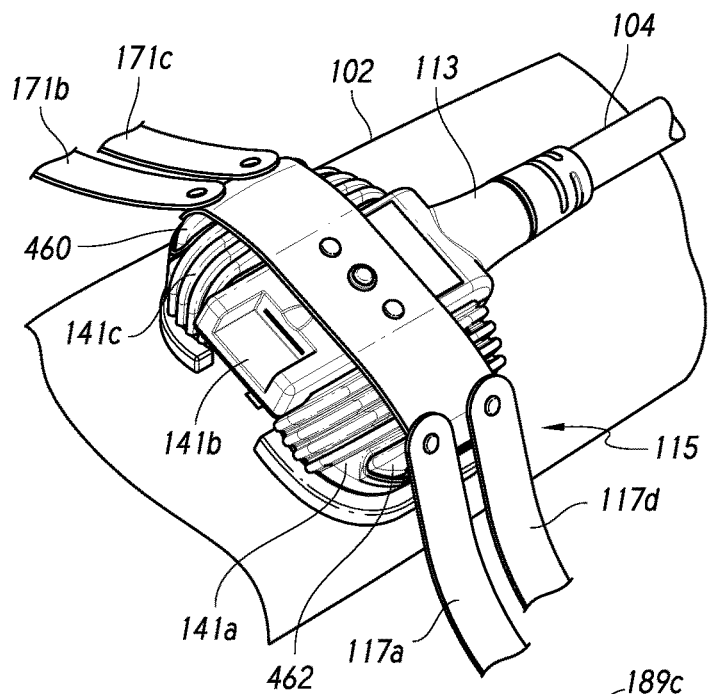

FIG. 15 is a view of the applicator 113 after it has been positioned on the subject in accordance with embodiments of the technology. The applicator 113 can be biased toward a treatment bend configuration suitable for application to the thigh. The illustrated strap assembly 115 is in an open configuration. The straps 117 can be wrapped around the subject's thigh 102 and coupled together to apply forces (indicated by arrows 450, 452 in FIG. 3) to end portions or shoulders 460, 462 (FIG. 3) of the cooling units 141a, 141c, respectively. The shoulders 460, 462 can have curved surfaces along which the strap assembly 115 can slide to allow rotation of the cooling units 141a, 141c. The straps 117 can be individually tensioned to pull the cooling units 141 toward the thigh 102. The straps 117 can be used to adjust the pressure distribution applied by the applicator 113 and can be independently positioned along the subject's specific anatomy. The applied pressure can cause the tissue to conform to the applicator 113 while the hinges 165 allow the applicator 113 to assume the general shape (e.g., curvature) of the body surface. The combination of conforming of the tissue and conforming of the applicator 113 results in a high amount of thermal contact, as well as a desired comfortable fit.

In some embodiments, a protective liner can prevent direct contact between the applicator 113 and the subject's skin to reduce the likelihood of cross-contamination between patients, minimize cleaning requirements for the applicator 113, etc. The protective liner can be a sheet, a sleeve, or other component constructed from latex, rubber, nylon, Kevlar®, or other substantially impermeable or semipermeable material. Further details regarding a patient protection device may be found in U.S. Patent Publication No. 2008/0077201. A liner or protective sleeve may be positioned between the absorbent and the applicator 113 to shield the applicator and to provide a sanitary barrier that is, in some embodiments, inexpensive and thus disposable.

Figure 16:
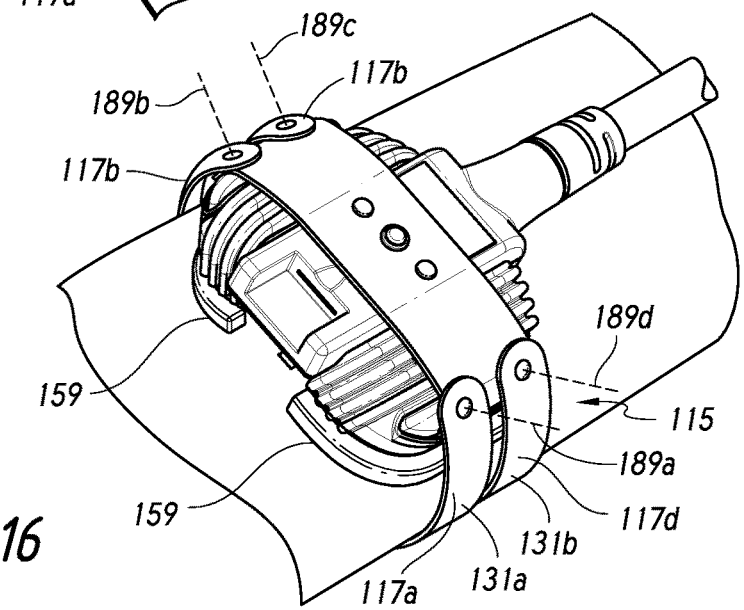
Figure 17:
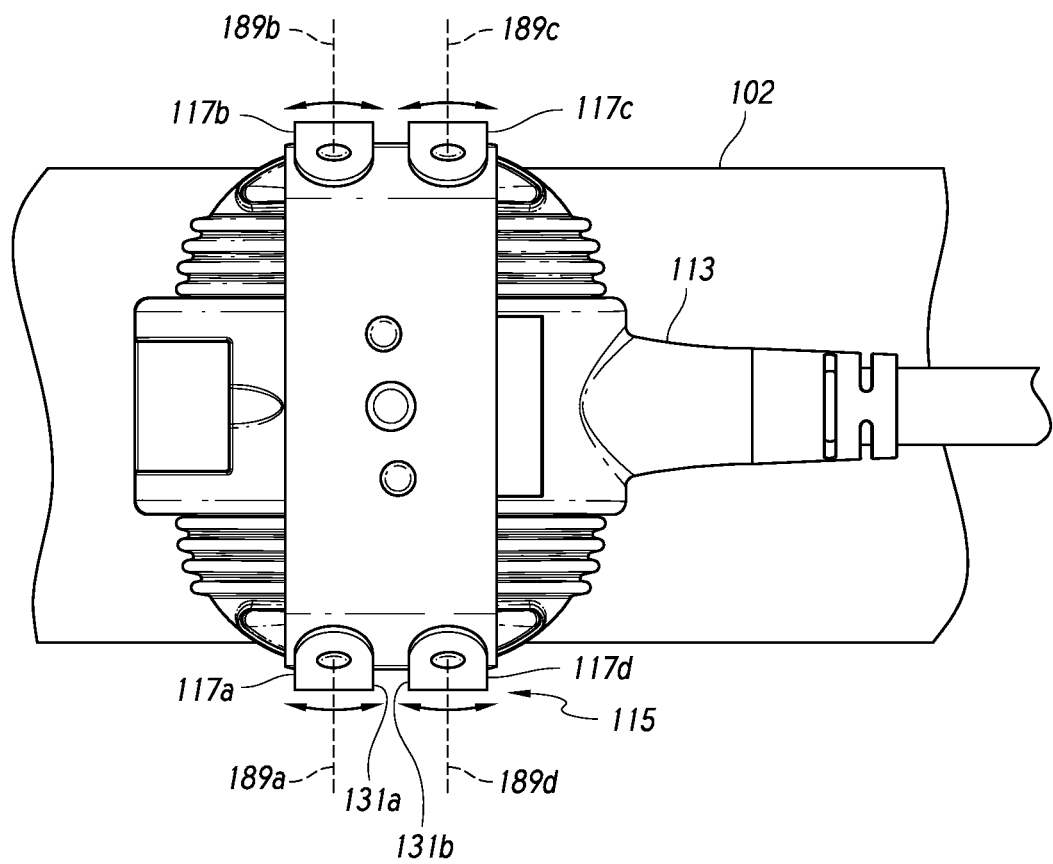

FIGS. 16 and 17 show the tensioned strap assembly 115 in a closed configuration. The four straps 117 can be periodically adjusted to achieve a desired conformable fit. As indicated by arrows in FIG. 17, the straps 117 can be rotated about axes of rotation 189a-d. In some embodiments, the axes of rotation 189a-d can extend through the applicator 113 and/or thigh 102, and the straps 117a, 117d can swivel to move apart to surround the subject's hip bone. For example, the hip bone can be positioned between the loops 131a, 131b for anchoring. The borders 159 (FIG. 16) can loosely or tightly hold the applicator 113 to prevent or limit sliding of the applicator 113 along the subject's skin without using, for example, a vacuum. As such, the applicator 113 can be used at treatment sites not suitable for drawing tissue into a traditional vacuum cup. Additionally, a target region can be treated without treating all, or most of, the circumference of the subject's body part. Thus, the applicator 113 can be used to comfortably treat local non-pinchable fat bulges.

To treat saddlebags, the applicator 113 can overlay the saddlebag such that the cooling unit 141a is generally positioned on an anterior side of the saddlebag 431 (FIG. 2) when the cooling unit 141b is positioned on a posterior side of a saddlebag and most of a circumference of the subject's thigh 102 is contacted by the flexible straps 117. For example, at least 60%, 70%, or 80% of the circumference of the thigh 102 can be contacted by the straps 117 rather than the applicator 113. The central cooling unit 141b can be positioned generally along the middle of the saddlebag to treat the saddlebag without treating a significant amount of surrounding tissue. The straps 117 can be tensioned to compress tissue, and as such, gaps between the applicator 113 and the subject can be reduced or eliminated. An operator can use the controller 114 (FIG. 1) to select and start treatment. The applicator 113 can cycle through, for example, segments of a prescribed treatment plan, which can include one segment for reducing the saddlebag on one side of the subject and another segment for reducing the other saddlebag. In other treatment plans, multiple applicators 113 can simultaneously treat saddlebags on opposite sides of the subject. Multiple applicators can also be used to simultaneously treat multiple sites. Any number of connectors can connect applicators to the control module. Each applicator can be held by a strap assembly and an applicator holder assembly. To sequentially treat multiple treatment sites, the same holder assembly (e.g., holder assembly 302) can be used at each treatment site or separate holder assemblies can be utilized at each separate treatment site.

During treatment, the controller 114 (FIG. 1) can determine whether a temperature or heat flux is sufficiently close to the target temperature or heat flux based, at least in part, on measurements from, for example, one or more temperature sensors (e.g., sensors 227 of FIG. 7). It will be appreciated that while a region of the body has been cooled or heated to the target temperature, in actuality that region of the body may be close but not equal to the target temperature, e.g., because of the body's natural heating and cooling variations. Thus, although the system 100 may attempt to heat or cool the tissue to the target temperature or to provide a target heat flux, a sensor may measure a sufficiently close temperature or heat flux. If the target temperature has not been reached, power can be increased or decreased to change the heat flux to maintain the target temperature or "set-point" selectively to affect targeted tissue. When the prescribed segment duration expires, the controller 114 may apply the temperature and duration indicated in the next treatment profile segment. In some embodiments, temperature can be controlled using a variable other than, or in addition to, power. For example, the controller 114 can provide cooling to the target region based on a predetermined or real-time determined treatment protocol. The cooling units 141 can first be cooled to cool the adjacent tissue of the target region to a temperature below 37° C. (e.g., to a temperature between about −40° C. to about 30° C., between about −30° C. to about 25° C., or between about −20° C. to about 20° C.). The controller 114 can execute programs for body contouring, treating cellulite, improving skin appearance, targeting glands, and/or performing other methods as described in, for example, U.S. patent application Ser. No. 14/611,127 entitled "TREATMENT SYSTEMS, METHODS, AND APPARATUS FOR IMPROVING THE APPEARANCE OF SKIN AND PROVIDING FOR OTHER TREATMENTS," U.S. patent application Ser. No. 14/611,052 entitled "TREATMENT SYSTEMS AND METHODS FOR TREATING CELLULITE AND FOR PROVIDING OTHER TREATMENTS," and International Patent Application No. PCT/US2015/013,971 entitled "TREATMENT SYSTEMS AND METHODS FOR AFFECTING GLANDS AND OTHER TARGETED STRUCTURES," which are incorporated herein in their entireties by reference.

FIG. 18 is a bottom view of an applicator 400 and an applicator holder assembly 402 ("holder assembly 402") in accordance with various embodiments of the present technology. FIG. 19 is a schematic cross-sectional view of the applicator 400 and the holder assembly 402. The applicator 400 includes four cooling units 410a-d movable relative to one another. As shown in FIG. 18, the cooling units 410a-d can define a generally elliptical or oval shaped continuous cooling surface 412. The holder assembly 402 has two borders 420 configured to surround all or most of the peripheries of the end cooling units 410a, 410d. The borders 420 can be arcuate members with a uniform or varying curvature, as viewed from above (see FIG. 18). Referring now to FIG. 19, each border 420 can have a receiving region 430 for receiving an outer portion 432 of the applicator 400. When the borders 420 are moved inwardly to engage the applicator 400 and adhesive 440 has been coupled to a subject, the outer portion 432 can be positioned in the receiving region 430 such that flanges 433 of the borders 420 extend along a backside 434 of the applicator 400. As such, the flanges 433 can help hold the applicator 400 against the subject.

FIG. 20 is a bottom view of an applicator 500 and an applicator holder assembly 502 ("holder assembly 502") in accordance with various embodiments of the present technology. FIG. 21 is a schematic cross-sectional view of the applicator 500 and holder assembly 502. The applicator 500 includes three cooling units 510a-c that define a generally continuous cooling surface 512. The cooling unit 510a includes rounded corners 514a, 515a, and the cooling unit 510c includes rounded corners 514c, 515c. The cooling unit 510b has a generally rectangular shape. The holder assembly 502 has a two borders 520 configured to surround all or most of the ends of the cooling units 510a, 510c. The borders 520 can be generally U-shaped, as viewed from above (see FIG. 20). Referring to FIG. 21, when the borders 520 are moved inwardly to engage the applicator 500 and adhesive 540 has been coupled to a subject's skin, flanges 533 can be positioned on a backside 534 of the applicator 500.

FIG. 22 is a bottom view of an applicator 600 and an applicator holder assembly 602 ("holder assembly 602") in accordance with various embodiments of the present technology. FIG. 23 is a schematic cross-sectional view of the applicator 600 and the holder assembly 602. The applicator 600 includes five cooling units 610a-e rotatable relative to one another. The cooling units 610a-e can define a generally continuous cooling surface 612 with a generally circular shape. The holder assembly 602 has four borders 620 configured to surround most of the periphery 643 of the applicator 600. The borders 620 can be partially circular, as viewed from above (see FIG. 22). When the borders 620 are moved inwardly to engage the applicator 600 and adhesive 640 has been coupled to a subject's skin, sidewalls 651 of the borders 620 can contact the periphery 643 of the applicator 600.

The applicators and cooling units disclosed herein can have cooling plates (e.g., heat-exchanging elements, such as heat-exchanging elements 149a-c of FIG. 4) that can be flat, curved (e.g., concave, convex, wavy, etc.), or the like. In some embodiments, the heat-exchanging elements disclosed herein can have radii of curvature in one or more directions (e.g., a radius of curvature in one direction, a first radius of curvature in a first direction and a second radius of curvature in a second direction, etc.). In one embodiment, a rigid or flexible heat-exchanging element can have a radius of curvature in a direction generally parallel to the length or width of its exposed surface. Additionally, each heat-exchanging element can have the same configuration (e.g., curvature). In other embodiments, the heat-exchanging elements can have different configurations (e.g., shapes, curvatures, etc.). Applicators disclosed herein can have one of more flat heat-exchanging elements and one or more non-planar or shaped heat-exchanging elements. For example, the heat-exchanging elements 141a, 141c (see FIG. 4) can be flat, and the heat-exchanging element 141b (see FIG. 4) can be non-planar (e.g., curved, partially spherical, partially elliptical, etc.). The shapes, dimensions, and properties (e.g., rigidity, thermal conductivity, etc.) of the heat-exchanging elements and other components of the applicators can be selected to achieve the desired interaction with the subject.

The retainer apparatuses, strap assemblies, and other components or features disclosed herein can be used with, or modified for use with, the applicator 400 (FIGS. 18 and 19), applicator 500 (FIGS. 20 and 21), and applicator 600 (FIGS. 22 and 23). For example, the retainer apparatus 191 discussed in connection with FIGS. 1-17 can be used with applicators 400, 500, 600. A wide range of different types of applicator retention devices may be used to hold applicators and may include restraints (e.g., straps) rotatably connected to a retainer or an applicator by coupling elements that can provide one or more degrees of freedom. The coupling elements can include, without limitation, pivots, pins, joints (e.g., ball joints), bearings, or other types of rotatable joints. The applicators disclosed herein can include additional features for providing a vacuum, energy (e.g., electrical energy, radiofrequency, ultrasound energy, thermal energy, etc.), and so forth. The treatment systems can include a pressurization device (e.g., a pump, a vacuum, etc.) that assists in providing contact between the applicator (such as via the interface layer or sleeve) and the patient's skin. For example, the applicator 113 discussed in connection with FIGS. 1-17 can provide mechanical energy to a treatment region. In one embodiment, each cooling unit 141 can include one or more vibrators (e.g., rotating unbalanced masses). In other embodiments, mechanical vibratory energy can be imparted to the patient's tissue by repeatedly applying and releasing a vacuum to the subject's tissue, for instance, to create a massage action during treatment. Further details regarding a vacuum type devices and operation may be found in U.S. Patent Application Publication No. 2008/0287839.

Each applicator system may be designed to treat identified portions of the patient's body, such as saddlebags, lovehandles, chin, cheeks, arms, pectoral areas, thighs, calves, buttocks, abdomen, back, and so forth. Applicators can be sufficiently conformable to achieve a desired amount of thermal contact. Strap assemblies can be configured configure to wrap around the subject's head to position applicators along the subject face. Strap assemblies configured to wrap around the subject's chest can hold the applicators along the subject's chest, abdomen, back, or the like. For example, the straps 117 of FIG. 1 can be sufficiently long to be applied about the subject's chest. The applicator 113 may be capable of providing a vacuum to massage tissue, inhibit or prevent movement of the applicator 113, or otherwise affect treatment. Exemplary components and features that can be incorporated into the applicators disclosed herein are described in, e.g., commonly assigned U.S. Pat. No. 7,854, 754 and U.S. Patent Publication Nos. 2008/0077201, 2008/ 0077211, 2008/0287839, 2011/0238050 and 2011/0238051. The applicators disclosed herein may be cooled using only coolant, only thermoelectric elements, or other suitable features. In further embodiments, the treatment systems disclosed herein may also include a patient protection device incorporated into the applicators to prevent directed contact between the applicator and a patient's skin and thereby reduce the likelihood of cross-contamination between patients and/or minimize cleaning requirements for the applicator. The patient protection device may also include or incorporate various storage, computing, and communications devices, such as a radio frequency identification (RFID) component, allowing for example, use to be monitored and/or metered. Exemplary patient protection devices are described in commonly assigned U.S. Patent Publication No. 2008/0077201.

Although noninvasive applicators are illustrated and discussed with respect to FIGS. 1-23, minimally invasive applicators may also be employed. As an example, one or more cryoprobes, electrodes, and/or other invasive components may be incorporated into the applicators disclosed herein and can be inserted directly into the targeted tissue (e.g., subcutaneous adipose tissue) to cool, freeze, or otherwise thermally process the targeted tissue.

The applicators, retainer systems, strap assemblies, and/or other components of the treatment systems disclosed herein can be included in a kit. In some embodiments, a kit includes single-use disposable components, such as a disposable retainer system, a disposable cryoprotection element, and/or a disposable holder assembly. The kit can also include instruction documentation containing information regarding how to (a) apply the composition to a target region and/or a heat-exchanging surface of the treatment applicator and (b) reduce a temperature of the target region such that lipid rich cells in the region are affected while preserving non-lipid rich cells proximate to a heat-exchanging surface.

E. Computing Environments

Figure 24:
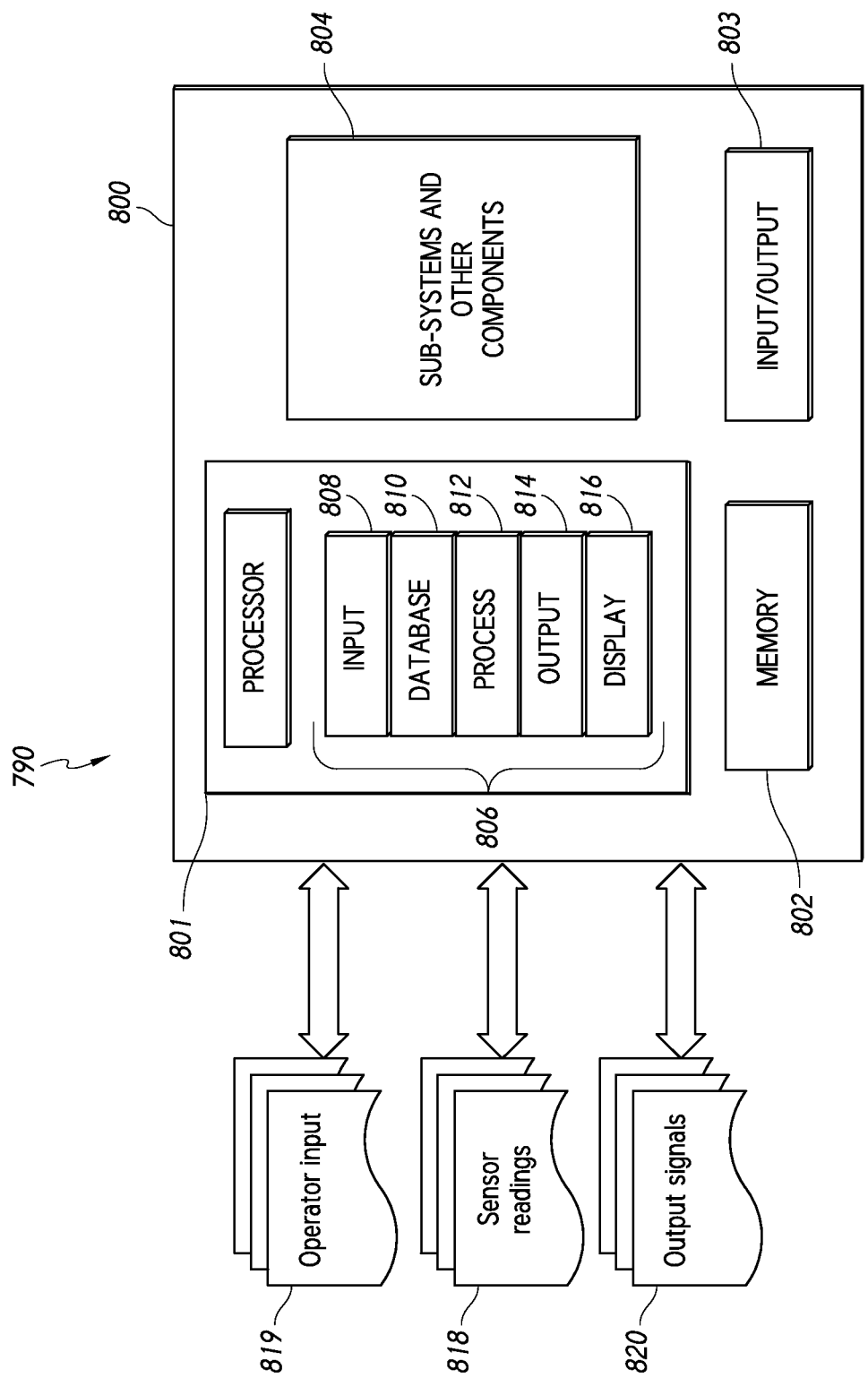
FIG. 24 is a schematic block diagram illustrating computing system software modules and subcomponents of a computing device in accordance with an embodiment of the technology.

FIG. 24 is a schematic block diagram illustrating subcomponents of a controller in accordance with an embodiment of the disclosure. The controller 790 can be the controller 114 of FIG. 1 or can be incorporated into the applicators or other components disclosed herein. The controller 790 can include a computing device 800 having a processor 801, a memory 802, input/output devices 803, and/or subsystems and other components 804. The computing device 800 can perform any of a wide variety of computing processing, storage, sensing, imaging, and/or other functions. Components of the computing device 800 may be housed in a single unit or distributed over multiple, interconnected units (e.g., though a communications network). The components of the computing device 800 can accordingly include local and/or remote memory storage devices and any of a wide variety of computer-readable media.

As illustrated in FIG. 24, the processor 801 can include a plurality of functional modules 806, such as software modules, for execution by the processor 801. The various implementations of source code (i.e., in a conventional programming language) can be stored on a computer-readable storage medium or can be embodied on a transmission medium in a carrier wave. The modules 806 of the processor can include an input module 808, a database module 810, a process module 812, an output module 814, and, optionally, a display module 816.

In operation, the input module 808 accepts an operator input 819 via the one or more input devices, and communicates the accepted information or selections to other components for further processing. The database module 810 organizes records, including patient records, treatment data sets, treatment profiles and operating records and other operator activities, and facilitates storing and retrieving of these records to and from a data storage device (e.g., internal memory 802, an external database, etc.). Any type of database organization can be utilized, including a flat file system, hierarchical database, relational database, distributed database, etc.

In the illustrated example, the process module 812 can generate control variables based on sensor readings 818 from sensors (e.g., sensors 227 of FIG. 7) and/or other data sources, and the output module 814 can communicate operator input to external computing devices and control variables to the controller. The display module 816 can be configured to convert and transmit processing parameters, sensor readings 818 (signals from sensors 227), output signals 820, input data, treatment profiles and prescribed operational parameters through one or more connected display devices, such as a display screen, printer, speaker system, etc.

In various embodiments, the processor 801 can be a standard central processing unit or a secure processor. Secure processors can be special-purpose processors (e.g., reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 802 can be standard memory, secure memory, or a combination of both memory types. By employing a secure processor and/or secure memory, the system can ensure that data and instructions are both highly secure and sensitive operations such as decryption are shielded from observation. In various embodiments, the memory 802 can be flash memory, secure serial EEPROM, secure field programmable gate array, or secure application-specific integrated circuit.

The input/output device 803 (e.g., device 118 of FIG. 1) can include, without limitation, a keyboard, a mouse, a stylus, a push button, a switch, a potentiometer, a scanner, an audio component such as a microphone, or any other device suitable for accepting user input and can also include one or more video monitor, a medium reader, an audio device such as a speaker, any combination thereof, and any other device or devices suitable for providing user feedback. For example, if the applicator 113 moves an undesirable amount during a treatment session, the input/output device 803 can alert the subject 101 and/or operator via an audible alarm. The input/output device 118 can be a touch screen that functions as both an input device and an output device. The control panel can include visual indicator devices or controls (e.g., indicator lights, numerical displays, etc.) and/or audio indicator devices or controls. The control panel may be a component separate from the input device 118 and/or output device 120, may be integrated with one or more of the devices, may be partially integrated with one or more of the devices, may be in another location, and so on. In alternative embodiments, the controller 114 can be contained in, attached to, or integrated with the applicator 113. In yet other embodiments, the various components can be fixedly installed at a treatment site. Further details with respect to components and/or operation of applicators, control modules (e.g., treatment units), and other components may be found in commonly-assigned U.S. Patent Publication No. 2008/0287839.

The controller 790 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference.

F. Conclusion

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above. While processes or blocks are presented in a given order, alternative embodiments may perform routines having stages, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the described technology.

Unless the context clearly requires otherwise, throughout the description, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

What is claimed is:

1. A wearable treatment system for cooling a target region in a subject, the treatment system comprising:
    a conformable applicator including a plurality of rotatable cooling units;
    a strap assembly connected to the conformable applicator and including a pair of straps each coupled to a respective pair of pivots located at opposite ends of the conformable applicator such that the straps position themselves with respect to the subject's body to maintain alignment of the conformable applicator relative to the target region when the strap assembly wraps about the subject and the conformable applicator, the strap assembly extends across backsides of each of the rotatable cooling units such that the strap assembly pushes front sides of each of the rotatable cooling units against the subject when the strap assembly is coupled to the conformable applicator and tensioned about the subject without tensioning at least two rotatable cooling units at opposite ends of the conformable applicator and beneath the strap assembly during use; and
    a compliant applicator holder assembly having a shape complementary to a shape of a periphery of the conformable applicator, wherein the compliant applicator holder assembly and the conformable applicator are not permanently connected to one another and are freely separable when the conformable applicator is held by the compliant applicator holder assembly adhered to the subject.

2. The treatment system of claim 1 wherein the straps are movable away from and/or toward one other to accommodate an anatomical feature of the subject when the straps wrap around a part of the subject's body.

3. The treatment system of claim 1 wherein the strap assembly in a closed configuration defines two loops for surrounding a body part of the subject and in an open configuration releases the body part of the subject, wherein the strap assembly is configurable to form two loops movable relative to one another to accommodate an anatomical feature of the subject, and wherein the strap assembly is operable to independently adjust sizes of the two loops.

4. A wearable treatment system for cooling a target region in a subject, the treatment system comprising:
    a conformable applicator including a plurality of rotatable cooling units;

a compliant applicator holder assembly having a shape complementary to a shape of a periphery of the conformable applicator, wherein the applicator holder assembly comprises adhesive that adheres to the subject's skin to define an applicator-receiving opening;

a strap assembly positioned relative to the conformable applicator and configured to position itself with respect to the subject's body to maintain alignment of the conformable applicator relative to the target region when the strap assembly is wrapped about the subject; and a pre-loaded spring assembly interconnecting the cooling units so as to pre-tension the cooling units into a predetermined bend angle relative to one another and to resist twisting of the cooling units relative to one another and to bias the conformable applicator to a treatment configuration for enhancing thermal contact with the subject for keeping the conformable applicator in the applicator-receiving opening while the compliant applicator holder assembly is not permanently connected to the conformable applicator such that the conformable applicator and the compliant applicator holder assembly are freely separable.

5. A treatment system for cooling a target region in a subject, the treatment system comprising:

an applicator including a plurality of cooling units configured to extract heat from the target region of the subject; and a compliant applicator holder assembly having a shape complementary to a shape of a periphery of the applicator such that the applicator holder assembly is configured to surround opposing ends of the applicator, wherein the applicator holder assembly and applicator are not permanently connected to one another and are freely separable, wherein the applicator holder assembly comprises adhesive and is configured to be applied to contoured regions of the subject to define an applicator-receiving opening dimensioned to receive the applicator, wherein when the applicator holder assembly is adhered to the subject's skin, the applicator is dimensioned to be moved into the applicator-receiving opening and the cooling units are rotatable relative to one another such that the applicator holder assembly surrounds the opposing ends of the applicator located in the applicator-receiving opening to thermally contact the subject's skin surrounded by the applicator holder assembly adhered to the subject's skin.

6. The treatment system of claim 5 wherein the applicator includes cooling units interconnected by pre-loaded spring assembly that bias the cooling units toward a non-planar configuration.

7. The treatment system of claim 5, further comprising a retainer apparatus having a closed configuration for holding the applicator in the applicator-receiving opening and an open configuration for releasing the subject, and wherein the retainer apparatus includes at least one adjustable length loop that extends circumferentially about a body part of the subject when the retainer apparatus is in the closed configuration, the applicator holder assembly being adjustable to adjust a configuration of the applicator-receiving opening.

8. The treatment system of claim 5 wherein the applicator holder assembly comprises:

a first border; and a second border, wherein the first and second borders surround opposing ends of the applicator when the first border is spaced apart from the second border and opposing ends of the applicator are received by the first and second borders.

9. The treatment system of claim 5 wherein the applicator holder assembly comprises a plurality of border members adherable to the subjects' skin such that the border members define the applicator-receiving opening with a shape complementary to a shape of the applicator.

10. The treatment system of claim 5 wherein the applicator holder assembly comprises:

a first border including a pair of first end portions and a first main body between the first end portions, wherein the first end portions are positioned on opposite sides of the applicator when a first end of the applicator faces the first main body; and a second border including a pair of second end portions and a second main body between the second end portions, wherein the second end portions are positioned on the opposite sides of the applicator when a second end of the applicator faces the second main body, wherein the second end of the applicator is opposite the first end of the applicator, wherein the applicator holder assembly is configured to hold the applicator when the applicator is in a non-planar configuration, wherein the applicator comprises:

a main cooling unit; and at least one cooling unit rotatably coupled to the main cooling unit.

11. A treatment system for cooling a target region in a subject, the treatment system comprising:

a compliant applicator holder assembly;

a conformable applicator including a first cooling unit and a second cooling unit, wherein the first cooling unit and the second cooling unit are rotatable relative to each other to conform to the subject;

a pre-loaded spring assembly interconnecting the first and second cooling units so as (a) to pre-tension the first and second cooling units into a predetermined bend angle relative to one another to achieve a non-planer treatment configuration for enhancing thermal contact with a subject's leg or torso and (b) to resist twisting of the first and second cooling units relative to one another; and a strap assembly configured to hold the conformable applicator in thermal contact with the subject's skin when the strap assembly is wrapped around the subject and the conformable applicator is surrounded by the compliant applicator holder assembly adhered to the subject, wherein the conformable applicator and the conformable applicator are freely separable.

12. The treatment system of claim 11, wherein the pre-loaded spring assembly biases the first and second cooling units toward the predetermined bend angle, which is from 25 degrees to 35 degrees, to bring the first and second cooling units into thermal contact with an outer thigh of the subject.

* * * * *